(12) United States Patent
Flieg et al.

(10) Patent No.: US 10,265,453 B2
(45) Date of Patent: *Apr. 23, 2019

(54) LIVER SUPPORT SYSTEM

(71) Applicant: GAMBRO LUNDIA AB, Lund (SE)

(72) Inventors: Ralf Flieg, Rangendingen (DE);
Stephan Aldinger, Rostock (DE);
Markus Storr, Filderstadt (DE); Bernd Krause, Rangendingen (DE)

(73) Assignee: GAMBRO LUNDIA A.B., Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/646,846

(22) PCT Filed: Nov. 5, 2013

(86) PCT No.: PCT/EP2013/073058
§ 371 (c)(1),
(2) Date: May 22, 2015

(87) PCT Pub. No.: WO2014/079681
PCT Pub. Date: May 30, 2014

(65) Prior Publication Data
US 2015/0273127 A1    Oct. 1, 2015

(30) Foreign Application Priority Data

Nov. 26, 2012 (EP) .................................... 12194166

(51) Int. Cl.
*A61M 1/16* (2006.01)
*A61M 1/26* (2006.01)
(Continued)

(52) U.S. Cl.
CPC ............ *A61M 1/1627* (2014.02); *A61M 1/16* (2013.01); *A61M 1/1621* (2014.02);
(Continued)

(58) Field of Classification Search
CPC .... A61M 1/16; A61M 1/1625; A61M 1/1627; A61M 1/1633; A61M 1/30; A61M 1/301;
(Continued)

(56) References Cited

U.S. PATENT DOCUMENTS 3,503,515 A    3/1970    Tomsic
4,784,768 A   11/1988    Mathieu
(Continued)

FOREIGN PATENT DOCUMENTS

EP          0341413       11/1989
EP          0 615 780 A1   9/1993
(Continued)

OTHER PUBLICATIONS

Burt, H. M., et al. "Ion-exchange resins as potential phosphate-binding agents for renal failure patients: effect on the physicochemical properties of resins on phosphate and bile salt binding", Journal of Pharmaceutical Sciences vol. 76, No. 5, 379-383 (1987).*
(Continued)

*Primary Examiner* — Katherine Zalasky
*Assistant Examiner* — Benjamin L Lebron
(74) *Attorney, Agent, or Firm* — Barnes & Thornburg LLP

(57) ABSTRACT

An artificial, extracorporeal system for liver replacement and/or assistance, comprises a liver dialysis device for conducting hemodialysis on a patient suffering from liver failure. The liver dialysis device comprises a first standard hollow fiber membrane dialyzer which does not allow passage of an essential amount of albumin over the membrane wall and which is perfused with the patient's blood, and a second hollow fiber membrane dialyzer which allows the passage of essential but defined amounts of albumin over the membrane wall and which receives the blood of the first standard hemodialyzer. The filtrate space is closed off from (Continued)

the lumen space of the hollow fibers and is populated by adsorbent material which may comprise one or more different adsorbents.

16 Claims, 12 Drawing Sheets

(51) Int. Cl.
| | |
|---|---|
| A61M 1/34 | (2006.01) |
| A61M 1/36 | (2006.01) |
| B01D 15/26 | (2006.01) |
| B01D 15/32 | (2006.01) |
| B01D 61/24 | (2006.01) |
| B01D 61/30 | (2006.01) |
| B01D 63/02 | (2006.01) |
| B01D 63/04 | (2006.01) |
| B01D 69/02 | (2006.01) |
| B01D 69/08 | (2006.01) |
| B01D 69/14 | (2006.01) |
| B01D 71/42 | (2006.01) |
| B01D 71/56 | (2006.01) |
| B01D 71/68 | (2006.01) |
| B01J 20/10 | (2006.01) |
| B01J 20/20 | (2006.01) |
| B01J 20/26 | (2006.01) |
| B01J 20/28 | (2006.01) |
| B01J 47/014 | (2017.01) |
| D01D 5/24 | (2006.01) |
| B01D 15/36 | (2006.01) |

(52) U.S. Cl.
CPC ........ *A61M 1/1633* (2014.02); *A61M 1/1696* (2013.01); *A61M 1/26* (2013.01); *A61M 1/34* (2013.01); *A61M 1/3472* (2013.01); *A61M 1/3475* (2014.02); *A61M 1/3486* (2014.02); *A61M 1/3679* (2013.01); *B01D 15/265* (2013.01); *B01D 15/325* (2013.01); *B01D 61/243* (2013.01); *B01D 61/30* (2013.01); *B01D 63/02* (2013.01); *B01D 63/021* (2013.01); *B01D 63/022* (2013.01); *B01D 63/023* (2013.01); *B01D 63/04* (2013.01); *B01D 63/046* (2013.01); *B01D 69/02* (2013.01); *B01D 69/08* (2013.01); *B01D 69/147* (2013.01); *B01D 71/42* (2013.01); *B01D 71/56* (2013.01); *B01D 71/68* (2013.01); *B01J 20/103* (2013.01); *B01J 20/20* (2013.01); *B01J 20/205* (2013.01); *B01J 20/261* (2013.01); *B01J 20/28016* (2013.01); *B01J 47/014* (2017.01); *A61M 1/3413* (2013.01); *A61M 1/3437* (2014.02); *A61M 2205/75* (2013.01); *A61M 2210/1071* (2013.01); *B01D 15/362* (2013.01); *B01D 15/363* (2013.01); *B01D 2311/06* (2013.01); *B01D 2311/2623* (2013.01); *B01D 2311/2626* (2013.01); *B01D 2313/40* (2013.01); *B01D 2325/12* (2013.01); *B01D 2325/20* (2013.01); *B01D 2325/36* (2013.01); *B01D 2325/38* (2013.01); *B01D 2325/42* (2013.01); *D01D 5/24* (2013.01)

(58) Field of Classification Search
CPC ...... A61M 1/303; A61M 1/34; A61M 1/3406; A61M 1/3417; A61M 1/3472; A61M 1/3486; A61M 2205/75; A61M 2210/1071; A61M 1/1621; A61M 1/1696; A61M 1/26; A61M 1/3413; A61M 1/3437; A61M 1/3475; A61M 1/3679; B01D 61/24; B01D 61/28; B01D 61/30; B01D 63/02; B01D 15/265; B01D 15/325; B01D 15/362; B01D 15/363; B01D 61/243; B01D 63/021; B01D 63/022; B01D 63/023; B01D 63/04; B01D 63/046; B01D 69/02; B01D 69/08; B01D 69/147; B01D 71/42; B01D 71/56; B01D 71/68; B01D 2311/06; B01D 2311/2623; B01D 2311/2626; B01D 2313/40; B01D 2325/12; B01D 2325/20; B01D 2325/36; B01D 2325/38; B01D 2325/42; B01J 20/103; B01J 20/20; B01J 20/205; B01J 20/261; B01J 20/28016; B01J 47/014; D01D 5/24

See application file for complete search history.

(56) References Cited

U.S. PATENT DOCUMENTS

| | | | | |
|---|---|---|---|---|
| 5,480,552 | A | * | 1/1996 | Soltys .................. B01D 61/147 210/500.23 |
| 5,919,370 | A | * | 7/1999 | Rottger .............. B01D 67/0013 210/490 |
| 6,497,675 | B1 | * | 12/2002 | Davankov ........... A61M 1/3472 210/433.1 |
| 6,709,598 | B1 | | 3/2004 | Pearl |
| 2003/0111414 | A1 | | 6/2003 | Baurmeister et al. |
| 2004/0035793 | A1 | * | 2/2004 | Legendre, Jr. ..... C12N 15/1006 210/656 |
| 2004/0069710 | A1 | | 4/2004 | Sirkar |
| 2005/0015040 | A1 | | 1/2005 | Wuepper et al. |
| 2005/0029193 | A1 | | 2/2005 | Matson et al. |
| 2006/0144782 | A1 | * | 7/2006 | Buck .................. B01D 67/0002 210/500.23 |
| 2007/0163950 | A1 | * | 7/2007 | Wechs .............. B01D 67/0011 210/500.41 |
| 2008/0185322 | A1 | | 8/2008 | Christmann et al. |
| 2009/0304677 | A1 | | 12/2009 | Ichim et al. |
| 2010/0004588 | A1 | | 1/2010 | Yeh et al. |
| 2010/0044312 | A1 | * | 2/2010 | Atti ..................... A61M 1/3472 210/638 |
| 2011/0040228 | A1 | * | 2/2011 | Radunsky ........... A61M 1/3413 604/5.04 |
| 2011/0094962 | A1 | | 4/2011 | Heinrich et al. |
| 2011/0208319 | A1 | * | 8/2011 | Laster ................. A61M 1/1678 623/23.65 |
| 2011/0218512 | A1 | | 9/2011 | Tullis et al. |
| 2012/0226258 | A1 | | 9/2012 | Otto et al. |
| 2012/0305487 | A1 | | 12/2012 | Beck et al. |

FOREIGN PATENT DOCUMENTS

| | | |
|---|---|---|
| EP | 1 257 333 | 8/2001 |
| EP | 1518870 | 3/2005 |
| EP | 1627941 | 2/2006 |
| EP | 1 875 956 A1 | 7/2006 |
| EP | 1 875 957 A1 | 7/2006 |
| EP | 1685862 | 8/2006 |
| EP | 2113298 | 11/2009 |
| EP | 2 380 610 A1 | 4/2010 |
| EP | 2281625 | 2/2011 |
| EP | 2 604 331 A1 | 12/2011 |
| EP | 2 735 360 A1 | 11/2012 |
| GB | 1470206 | 4/1977 |
| WO | 9108782 | 6/1991 |
| WO | 99/25726 A1 | 5/1999 |
| WO | 9925726 | 5/1999 |
| WO | 0067885 | 11/2000 |
| WO | 01/60477 A2 | 8/2001 |
| WO | 2004/003268 A1 | 1/2004 |
| WO | 2004014315 | 2/2004 |
| WO | 2004056460 | 7/2004 |

(56) References Cited

FOREIGN PATENT DOCUMENTS

| WO | WO 2011131534 A1 * | 10/2011 | ............. A61M 1/16 |
| WO | 2012/142180 A1 | 10/2012 | |
| WO | 2012142180 | 10/2012 | |

OTHER PUBLICATIONS

Boschetti de Fierro, A., et al. "Extended characterization of a new class of membranes for blood purification: the high cut-off membranes", International Journal of Artificial Organs, vol. 36 No. 7, 455-463 (2013). Published online May 10, 2013.*

Fresenius Medical Care, "Ci—Ca CVVHD with Ultraflux EMiC2". Sep. 10, 2010.*

Gambro Lundia AB, "The Prismaflex eXeed system and the septeX set". May 5, 2009.*

Gambro Lundia AB, "Polyflux Revaclear single-use high-flux dialyzer", Feb. 16, 2012.*

Stadlbauer, V., et al., "Removal of bile acids by two different extracorporeal liver support systems in acute-on-chronic liver failure", ASAIO Journal, 53, pp. 187-193 (2007).*

Kirkland, J., and DeStefano, J., "The art and science of forming packed analytical high-performance liquid chromatography columns", Journal of Chromatography A, 1126, pp. 50-57 (2006).*

PCT International Search Report, International Application No. PCT/EP2013/073056, dated Dec. 20, 2013, 4 pages.

Aimar et al, A Contribution to the Translation of Retention Curves into Pore Size Distributions for Sieving Membranes, Journal of Membrane Science, 54, (1990), pp. 321-338.

Boldt, Use of Albumin: An Update, British Journal of Anaesthesia 104 (3): doi: 10.1093/bja/aep393, (2010), pp. 246-284.

Cardiovascular Implants and Extracorporeal Systems—Haemodialysers, Haemodiafilters, Haemofilters and Haemoconcentrators, International Standard, Reference No. ISO 8637, Third edition Jul. 1, 2010, 28 pages.

Stauber et al, MARS and Prometheus in Acute-on-Chronic Liver Failure: Toxin Elimination and Outcome, Transplantationsmedizin, (2010), 22. Jahrg., S., pp. 333-338.

Honore et al, Hemofiltration, Adsorption, Sieving and the Challenge of Sepsis Therapy Design, (2002), 4 pages, BioMed Central Ltd (Print ISSN 1364-8535; Online ISSN 1466-609X), http://ccforum.com/content/6/5/394.

Metallic powders—Determination of tap density (ISO 3953:2011); German version EN ISO 3953:2011, 2011, 9 pages.

PCT International Search Report, International Application No. PCT/EP2013/073045, dated Feb. 12, 2014, 3 pages.

PCT International Search Report, International Application No. PCT/EP2013/073058, dated Mar. 13, 2014, 6 pages.

International Search Report from related WO 2014/079679 dated Feb. 4, 2014, 3 pages.

* cited by examiner

LIVER SUPPORT SYSTEM

CROSS REFERENCE TO RELATED APPLICATIONS

This application is the U.S. national phase of PCT/EP2013/073058 filed Nov. 5, 2013. PCT/EP2013/073058 claims priority under the Paris Convention to European patent application 12194166.0, filed Nov. 26, 2012. EP 12194166.0 and PCT/EP2013/073058 are hereby incorporated herein in their entireties by this reference.

TECHNICAL FIELD

The present disclosure relates to an artificial, extracorporeal system for liver replacement and/or assistance, comprising a liver dialysis device for conducting hemodialysis on a patient suffering from liver failure, which is characterized in that it comprises a first standard hollow fiber membrane dialyzer which does not allow passage of an essential amount of albumin over the membrane wall and which is perfused with the patient's blood, and a second hollow fiber membrane dialyzer which allows the passage of essential but defined amounts of albumin over the membrane wall and which receives the blood of the first standard hemodialyzer and wherein the filtrate space is closed off from the lumen space of the hollow fibers and is populated by adsorbent material which may comprise one or more different adsorbents. The system can be used for the treatment of acute liver failure and acute-on-chronic liver failure.

DESCRIPTION OF THE RELATED ART

There is a need to develop or improve artificial systems and devices for liver replacement and/or assistance which are used to either support patients with borderline function of their liver until their liver regenerates or until a donor liver is obtained for transplantation. Several systems are known in the prior art today which serve this purpose. In principle, such liver support, often also referred to as liver dialysis, is a detoxification treatment and is used for patients with various liver disorders, such as, for example, hepatorenal syndrome, decompensated chronic liver disease, acute liver failure, graft dysfunction after liver transplantation, liver failure after liver surgery, secondary liver failure, multi organ failure or intractable pruritus in cholestasis. It is similar to hemodialysis and based on the same principles. Like a bioartificial liver device, it is a form of artificial extracorporeal liver support.

The so-called hepatorenal syndrome (HRS) is a life-threatening medical condition that consists of rapid deterioration in kidney function in individuals with cirrhosis or massive liver failure. HRS is usually fatal unless a liver transplant is performed, although various treatments, such as dialysis, can prevent advancement of the condition.

HRS can affect individuals with cirrhosis (regardless of cause), severe alcoholic hepatitis, or massive hepatic failure, and usually occurs when liver function deteriorates rapidly because of an acute injury such as an infection, bleeding in the gastrointestinal tract, or overuse of diuretic medications. HRS is a relatively common complication of cirrhosis, occurring in 18% of cirrhotics within one year of their diagnosis, and in 39% of cirrhotics within five years of their diagnosis. Deteriorating liver function is believed to cause changes in the circulation that supplies the intestines, altering blood flow and blood vessel tone in the kidneys. The renal failure of HRS is a consequence of these changes in blood flow, rather than direct damage to the kidney. Two forms of hepatorenal syndrome have been defined: Type 1 HRS entails a rapidly progressive decline in kidney function, while type 2 HRS is associated with ascites (fluid accumulation in the abdomen) that does not improve with standard diuretic medications.

For example, the risk of death in hepatorenal syndrome is very high; the mortality of individuals with type 1 HRS is over 50% over the short term. The only long-term treatment option for the condition is liver transplantation. As a short-term treatment option before transplantation, liver dialysis may turn out to be vitally important for the patient.

A critical issue of the clinical syndrome in liver failure is the accumulation of toxins not cleared by the failing liver. Based on this hypothesis, the removal of lipophilic, albumin-bound substances such as bilirubin, bile acids, metabolites of aromatic amino acids, medium-chain fatty acids and cytokines should be beneficial to the clinical course of a patient in liver failure.

In liver dialysis systems such as the MARS® system blood is cleansed in an extracorporeal circuit that is a combination of both kidney and liver dialysis. Established methods for kidney dialysis alone are not applicable for liver failure because kidney dialysis removes water-soluble toxins only. The liver normally removes albumin bound toxins. Albumin is a protein found in the blood that carries water insoluble substances including toxins. For this reason, systems like the MARS® system make use of exogenous human albumin to cleanse the blood because the albumin removes the toxins which are bound to the endogenous albumin in the blood that the aqueous solution in kidney dialysis cannot remove, such as unconjugated bilirubin, bile acids, hydrophobic amino and fatty acids. A significant portion of toxins are water-soluble molecules of low- and middle-molecular weight, the concentration of which may be increased by hepatic failure and renal failure. These molecules can effectively be removed by hemodialysis. The MARS® system is thus thought to replace the detoxification function of the liver with regard to water-soluble and albumin-bound toxins. The principles of this system are already described in EP 0 615 780 A1.

The patient's blood in the current MARS® system is passed into a hollow fiber membrane hemodialyzer. The dialysate side of the dialyzer provides for clean human albumin that acts as a dialysate. As the patient's blood moves along the membrane, water-soluble and protein bound toxins in the blood are transported through the membrane and into the dialysate albumin solution on the other side. The membrane is impermeable to albumin and to other valuable proteins such as hormones and clotting factors, keeping them in the patient's circulation. The cleansed blood then returns to the patient. Meanwhile, the albumin solution carrying the toxins is recycled by passing first through a low-flux dialyzer. This process removes water-soluble substances from the albumin solution. The albumin then passes through an activated carbon adsorber and, after passing a filter which removes carbon particles, passes through an anion exchanger that removes toxins bound to albumin. The recycled albumin can then again enter the dialyzer and bind again to toxins which can thus be removed from the patient's blood. The MARS® system, though being effective, is relatively complex and requires that exogenous albumin is fed into the system, which also renders the system comparatively expensive.

Another known liver support system, the Prometheus® system, (FPSA, fractionated plasma separation and adsorption) is based on fractionated plasma separation across an albumin-permeable filter (AlbuFlow®) and high-flux dialysis in the blood circuit. The system utilizes a so-called AlbuFlow® membrane, which is permeable for larger proteins such as albumin. In this system the blood is first pumped through the AlbuFlow® filter that retains blood cells and large protein molecules. The blood liquid, or plasma, along with albumin and smaller protein molecules is then fed through two adsorbers that separate toxins from the albumin and bind them. Following adsorption, the blood plasma with the detoxified albumin is joined with the blood cells retained by the AlbuFlow filter. Finally, the blood is dialyzed to remove the remaining water-soluble toxins, and the filtered blood is then reintroduced into the patient. The system does not require exogenous albumin in the secondary circuit since endogenous albumin enters the secondary circuit via the AlbuFlow® membrane. Still, the Prometheus® system requires plasma fractionation and also encompasses several components, rendering also this system relatively complex.

Another approach, which is referred to as "SEPET", is based on selective plasma filtration which involves removing from a patient's blood a specific plasma fraction containing substances (including toxic substances) within a specific molecular weight range. The method has been described, for example, in WO 2004/014315 (A2).

It would be extremely desirable to reduce the complexity of the respective existing systems and/or improve the efficiency of liver toxin removal, especially with regard to the elimination of certain unwanted molecules, such as unconjugated bilirubin, bile acids and/or IL-6. It would be especially important to devise a method or device which allows for the efficient removal of protein-bound liver toxins. It is known that the current systems have limitations with regard to their elimination performance concerning strongly bound toxins, such as unconjugated bilirubin. Also, the accumulation of pro-inflammatory cytokines in acute liver failure is associated with a high mortality. IL-6, IL-1ß and TNF are known to induce massive necrotic inflammation of liver tissue.

The applicants have now developed a device for the treatment of liver failure which is simple and able to dispense with plasma fractionation, exogenous albumin and extra components such as adsorber cartridges, and at the same time achieves a significantly improved elimination performance for a variety of liver toxins. In a first step, the patient's blood is perfused through a standard hemodialyzer, such as, for example, a high-flux dialyzer as it is known in the art. This first step, which may in principle also be performed as a second step, serves for removing water-soluble toxins which already reduce the toxin load in the blood which is then perfused through a second dialyzer which is focused on the adsorption of toxins which would not be efficiently removed by standard hemodialysis. In a second step, optionally also in a first step, the cleansed blood which has left the first dialyzer enters the hollow fibers of a second filter device, which comprises a membrane which allows for the passage of an essential, but limited amount of albumin through the membrane wall. The albumin, which together with toxins bound thereto and smaller blood components that could not be removed by the high-flux dialyzer passes into the filtrate space of the dialyzer, is contacted there with certain adsorbents which populate the filtrate space of the device and which serve to remove protein-bound toxins, hydrophobic toxins and water-soluble toxins, all of which can be generically referred to as "liver toxins". The filtrate space is in fluid communication only with the lumen space of the hollow fibers. Accordingly, all components which were not adsorbed or bound by the particulate material in the filtrate space can again enter the lumen space of the hollow fibers and leave the dialyzer together with the blood and be directly returned to the patient.

The new liver dialysis device thus combines the functions of several of the aforementioned components of the known systems. At the same time, the new device is able to significantly improve the detoxification efficiency of the system. In particular, strongly albumin bound liver toxins, such as unconjugated bilirubin, bile acid and inflammatory cytokines such as interleukin 6 (IL-6) are removed with increased efficiency. The device further does not require any specifically adapted dialysis machine. The invention thus provides an improved and at the same time less complex system for the removal of liver toxins, specifically albumin-bound liver toxins from blood in extracorporeal liver support systems for the treatment of liver failure.

Hollow fiber filter modules which comprise particulate material on the filtrate side are known in the art. Examples for devices which make use of this principle are described, for example, in US 2011/0218512 A1, which relates to antiviral therapy methods comprising passing blood or plasma through a lectin affinity hemodialysis device. In the device, blood is passed through the lumen of a hollow fiber membrane, wherein lectins are located in the extraluminal space of the cartridge, which accepts and immobilizes the viruses. US 2009/0304677 A1 relates to methods for removing microvesicular particles such as exosomes from blood, wherein, in one specific embodiment, the blood is run through an extracorporeal circulation circuit that uses a hollow fiber cartridge. However, no such filter devices have become known so far which combine specific hollow fiber membranes allowing for a defined amount of albumin to pass the membrane wall, on the one hand, and active, particulate material on the filtrate side of the membrane on the other hand, thus combining, in one device, several functionalities which otherwise have to be served with several devices.

Also, while certain liver dialysis systems are known in the art which serve to remove certain toxins which go hand in hand with liver failure, no such systems have become known that combine standard high-flux dialyzers in line with an integrated dialyzer such as described before, both located in the blood circuit. The present invention describes such devices for the first time and also describes their use in liver support therapies.

SUMMARY

The present invention is directed to a new and improved liver support system for the treatment of liver failure. The liver support system is an extracorporeal system comprising components for conducting hemodialysis on a patient suffering from liver failure and is characterized in that it comprises a first standard hollow fiber membrane dialyzer (1) which does not allow passage of an essential amount of albumin over the membrane wall and which is perfused with the patient's blood, and a second hollow fiber membrane dialyzer (2) which allows the passage of certain defined amounts of albumin over the membrane wall, wherein the filtrate space is closed off from the lumen space of the hollow fibers and is populated by particulate material which comprises one or more different adsorbents.

The present invention is also directed to a hollow fiber membrane dialyzer (2) (see FIGS. 1 and 2) for the extracorporeal treatment of blood or blood products (herein generally and commonly referred to as "blood", if not indicated otherwise), comprising a cylindrical filter housing, a bundle of essentially parallel hollow fiber membranes (3b) which may be straight or ondulated and which are distributed longitudinally within the housing, a filtrate space (4b), which is closed off from the lumen space of the hollow fiber membranes (3b) and which optionally is in fluid communication with an inlet means (10b) and optionally an outlet means (11b). The filtrate space (4b) is populated with particulate material (5) comprising one or more adsorbents which serve to bind or adsorb, from the permeate having passed the hollow fiber membrane wall, toxins which accumulate in incidences of liver failure. The dialyzer further comprises an inlet means (7b) for feeding the blood which may be received from the patient or from hemodialyzer (1) into the lumen space of the hollow fiber membranes (3b), and an outlet means (8b) for removing the treated blood from the lumen of the hollow fiber membranes (3), which is then returned to the patient or passed on to dialyzer (1).

The present invention is also directed to improving the elimination of unwanted compounds from blood in incidences of liver failure with a liver support system according to the invention. This is achieved by incorporating into the hollow fiber membrane dialyzer (2) a membrane (3b) which is characterized by a molecular weight cut-off in water, based on dextran sieving coefficients, of between 170 and 320 kD and a molecular weight retention onset in water, based on dextran sieving coefficients, of between 10 and 20 kD. Such membrane will allow a sufficient amount of albumin and any toxin which may be bound thereto to pass the membrane wall and get in contact with the particulate material (5) which populates the filtrate space (4b) of the dialyzer. The cleansed permeate comprising, for example, the albumin with essentially no toxins bound thereto can leave the filtrate space by re-entering the lumen space of the hollow fiber membranes from where it can leave the dialyzer (2) through outlet means (8b) and can be returned to the patient.

The present invention is also directed to a hollow fiber membrane dialyzer (2), wherein the membrane allows passage of substances having a molecular weight of up to 45 kD with a sieving coefficient measured according to ISO 8637 in whole blood of between 0.1 and 1.0. The membrane allows passage of albumin having a molecular weight of about 68 kD with a sieving coefficient of between 0.1 and 0.3 according to ISO8637 with bovine plasma (60 g/l), 37° C., $Q_B$ max and UF 20%. According to one embodiment of the invention, the sieving coefficient of albumin is about 0.2.

The present invention is also directed to a hollow fiber membrane dialyzer (2), wherein the membrane has a sieving coefficient for albumin of between 0.05 and 0.2 according to ISO8637 with bovine plasma (60 g/l), 37° C., $Q_B$ max and UF 20%.

The present invention is also directed to a hollow fiber membrane dialyzer (2), wherein the hollow fiber membrane (3b) allows an essential concentration equalization of albumin between the blood side and the filtrate side of dialyzer (2) after between 0.8 and 1.2 hours of treatment at blood flow rates of between 200 to 500 ml/min. The term "essential" in this context refers to the fact that such concentration equalization may be reached only in parts of the dialyzer, i.e. in about the middle third of the dialyzer.

The present invention is also directed to a hollow fiber membrane dialyzer (2), wherein the one or more adsorbents in filtrate space (4b) are chosen from the group consisting of charged, hydrophilic and uncharged, hydrophobic particulate material. The charged material comprises ion exchange particles such as, for example, anion exchange or cation exchange material. The hydrophobic material comprises activated carbon, carbon nanotubes, hydrophobic silica, styrenic polymers, polydivinylbenzene polymers and styrene-divinylbenzene copolymers. The particulate material in the filtrate space may consist of one or more hydrophilic, charged adsorbents or one or more uncharged, hydrophobic adsorbents, or may consist of a mixture of one or more hydrophilic adsorbents and one or more hydrophobic adsorbents.

The present invention is also directed to the use of a liver support system according to the invention for the removal of liver toxins from fluids in extracorporeal therapies.

BRIEF DESCRIPTION OF THE DRAWINGS

FIG. 7 shows the results for the removal of creatinine which have been obtained in Example 3 with a test setup according to FIG. 6.

FIG. 8 shows the results for the removal of ammonium which have been obtained in Example 3 with a test setup according to FIG. 6.

FIG. 9 shows the results for the removal of chenodeoxycholic acid (CDCA) which have been obtained in Example 3 with a test setup according to FIG. 6.

DETAILED DESCRIPTION

Figure 3:
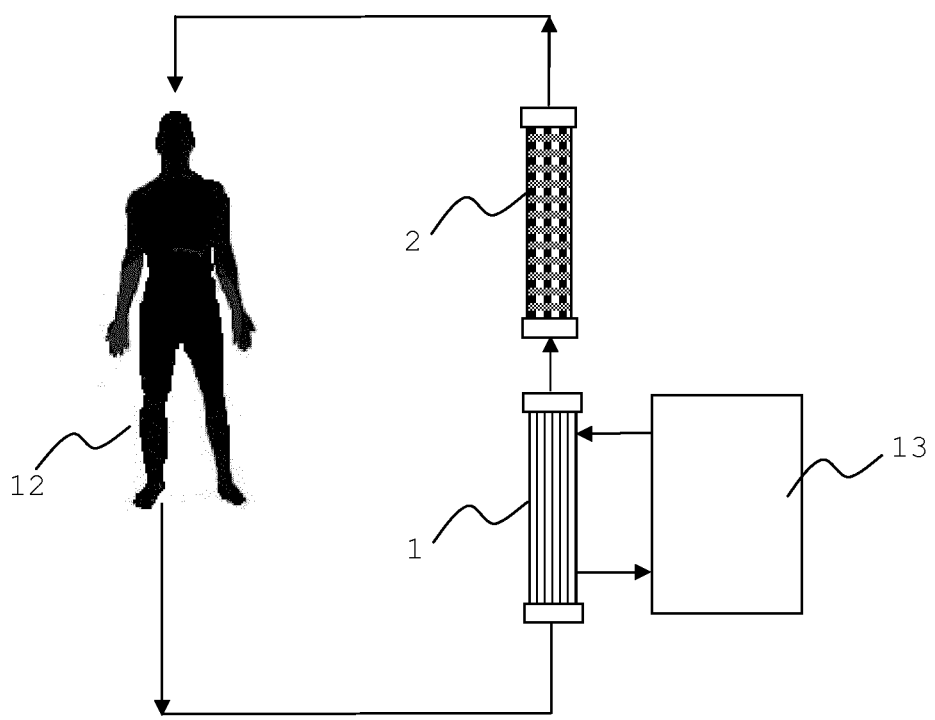
FIG. 3 shows a very schematic representation of the liver support system of the present invention. Blood is drawn from the patient (12) for its extracorporeal treatment. In the present Figure the blood first enters dialyzer (1) and thereafter perfuses dialyzer (2). The hollow fiber membrane dialyzers (1) and (2) are described in more detail in FIG. 1. The dialysis machine used within the system is displayed as (13).

The present invention is directed to a liver support system (FIG. 3) for the treatment of a patient suffering from liver failure, which is characterized in that it comprises, in the blood circuit, a first hollow fiber membrane dialyzer (1) which does not allow passage of an essential amount of albumin over the membrane wall and which is perfused with the patient's blood (6) which enters the dialyzer at inlet port (7a), and wherein dialysate solution (9) is passed in a continuous flow through the filtrate space (4a) in a direction opposite to the blood flow within the hollow fibers (3a), and a second hollow fiber membrane dialyzer (2) which allows the passage of certain amounts of albumin over the membrane wall and which receives the treated blood (6) from the patient (12) or from first dialyzer (1) through inlet port (7b), wherein the filtrate space (4b) is closed off from the lumen space of the hollow fiber membranes (3b) and is not perfused by any dialysis solution, and wherein a particulate material (5), comprising hydrophilic material and/or hydrophobic material, populates the filtrate space of the hollow fiber membrane dialyzer (2). In principle, it is possible to first pass the blood through hollow fiber membrane dialyzer (2) and, thereafter, through hollow fiber membrane dialyzer (1). However, it may be advantageous to first remove the water-soluble toxins by standard hemodialysis, thus reducing the toxin load of the blood before it enters dialyzer (2). Dialyzer (2) mainly serves for the removal of toxins which typically emerge in liver failure situations, especially protein-bound (albumin-bound) toxins which are lipophilic (hydrophobic), and which cannot be removed with dialysis systems which are available for renal dialysis and the removal of standard uremic toxins.

In the context of the present invention, the expression "essential amounts of albumin" or "certain amounts of albumin" means that the hollow fiber membrane of dialyzer (2) allows passage of albumin with a sieving coefficient measured according to ISO8637 with bovine plasma (protein level 60 g/l), 37° C., $Q_B$ max (generally between 200 and 500 ml/min) and UF 20%, of between 0.1 and 0.3. Thus, the albumin together with the liver toxins which may be bound thereto will get into contact with the particulate material in the filtrate space, whereby said bound and unbound toxins can effectively be removed. At the same time, the specific hollow fiber membrane (3b) which is used in dialyzer (2) prevents the passage of still larger proteins such as, for example, coagulation factors such as fibrinogen and other components which should essentially be retained in the blood of the patient. Dialyzer (1) does not allow the passage of essential amounts of albumin over the membrane wall, which means that the sieving coefficient for albumin as measured according to ISO8637 with bovine plasma (protein level 60 g/l), 37° C., is below 0.01 at $Q_B$max and UF20%.

The hollow fiber membrane dialyzer (1) which is used in a liver support system according to the invention may be a dialyzer as currently used for hemodialysis, haemofiltration or hemodiafiltration in extracorporeal treatments of renal dialysis patients. According to one aspect of the present invention, the hollow fiber membranes which can be used in a hollow fiber membrane dialyzer (1) are so-called low-flux membranes, even though preference is given to the high-flux membrane dialyzers further described below. Low-flux dialyzers are generally characterized by a lower permeability compared to high-flux membranes. Low-flux membranes can be characterized by having an UF coefficient of below 15 mL/h/mm Hg and a ß2-microglobulin clearance of below 10 ml/min. Based on dextran sieving coefficients, low-flux membranes may further be characterized by a molecular weight cut-off (MWCO) (kg/mol) of 10-20 and a molecular weight retention onset (MWRO) of between 2 and 4 kD. The MWRO is defined as the lowest molecular weight for which the sieving coefficient is 0.9. The water permeability of low-flux membranes generally is in the range of from $2\text{-}5 \cdot 10^{-4}$ cm/(bar·s) (with 0.9 wt.-% NaCl at 37±1° C. and $Q_B$ 100-500 ml/min).

According to one embodiment of the invention, the hollow fiber membranes which can be used in a hollow fiber membrane dialyzer (2) are so-called high-flux membranes. The term "high-flux" is sometimes used indistinctly. High-flux membranes are generally characterized by their high permeability compared to low-flux membranes, which increases the in vitro clearance of certain marker molecules such as vitamin B12 having a molecular weight of about 1.4 kD. High-flux membranes are also characterized by their ability to remove solutes of higher molecular weight, such as β2-microglobulin (11.8 kD). In the context of the present invention, the term "high-flux" and "high-flux membrane", respectively, refers to membranes having an UF coefficient of >15 mL/h/mm Hg, wherein the UF coefficient determines quantity of pressure that must be exerted across dialysis membrane (transmembrane pressure) to generate a given volume of ultrafiltrate per unit time, a ß2-microglobulin clearance of >20 mL/min, preferably between 20 to 40 mL/min as measured in conventional HD with $Q_B$ 300-400 ml/min and $Q_D$ 500 ml/min for membrane areas between about 1.7 and 2.1 m², and a mass transfer coefficient ($K_oA$) of >450 mL/min. A high-flux membrane in the context of the present invention is further defined by a water permeability of the membrane of $40\text{-}90 \cdot 10^{-4}$ cm/(bar·s) (with 0.9 wt.-% NaCl at 37±1° C. and $Q_B$ 100-500 ml/min). The albumin loss of a high-flux membrane in the context of the present invention is <0.5 g in conventional HD, after 4 h and $Q_B$ of 250 ml/min and $Q_D$ 500 ml/min. High-flux membranes are further characterized by a pore radius of about 3.5-5.5 nm compared to low-flux membranes with a pore radius of about 2-3 nm and high cut-off membranes with a pore radius 8-12 nm, as based on dextran sieving coefficients determined as described, for example, in U.S. patent application Ser. No. 13/477,473. Based on said dextran sieving coefficients, high-flux membranes may further be characterized by a molecular weight cut-off (MWCO) (kg/mol) of 25-65 and a molecular weight retention onset (MWRO) of between 5 and 10 kD.

High-flux and low-flux dialyzers can be made from various materials, comprising cellulosic and synthetic materials. According to one embodiment of the present invention, the membrane of the hollow fiber membrane dialyzers (1) is comprised of at least one hydrophobic polymer and at least one hydrophilic polymer. According to one embodiment of the invention, the hydrophobic polymer is chosen from the group consisting of polyarylethersulfone (PAES), polypropylene (PP), polysulfone (PSU), polycarbonate (PC), polyacrylonitrile (PAN), polyamide (PA) polytetrafluorethylene (PTFE) or combinations thereof, and the at least one hydrophilic polymer is chosen from the group consisting of polyvinylpyrrolidone (PVP), polyethyleneglycol (PEG), polyvinylalcohol (PVA), and copolymer of polypropyleneoxide and polyethyleneoxide (PPO-PEO). According to yet another embodiment of the invention, high-flux membranes used in hollow fiber membrane dialyzers (1) are comprised of a copolymer of acrylonitrile and sodium methallyl sulfonate and are optionally coated, on their surface, with polyethyleneimine (PEI), preferably high molecular weight PEI, and may further optionally have grafted thereon heparin.

According to one embodiment of the invention, dialyzer (1) comprises a membrane based on polyethersulfone, polyamide, and polyvinylpyrrolidone having an asymmetric 3-layer structure and showing a hydraulic permeability (Lp) of about $5 \times 10^{-4}$ cm/bars. Such membrane is contained, for example, in filters sold by Gambro Lundia AB under the trade name Polyflux® P21L. Another example for a fiber that can be used in a dialyzer (1) according to the present invention is a membrane comprising polyethersulfone, polyamide, and polyvinylpyrrolidone having an asymmetric 3-layer structure and showing a hydraulic permeability Lp of about $80 \times 10^{-4}$ cm/bars. Such membrane is contained, for example, in filters sold by Gambro Lundia AB under the trade name Polyflux® P210H. Another example for a fiber that can be used in a dialyzer (1) according to the invention is a membrane comprising polyarylethersulfone and polyvinylpyrrolidone and having an asymmetric 3-layer structure and showing a hydraulic permeability (Lp) of about $80 \times 10^{-4}$ cm/bars. Such membrane is contained, for example, in filters sold by Gambro Lundia AB under the trade name Polyflux® Revaclear. According to another embodiment of the invention, the liver support system of the invention comprises, as dialyzer (1), the oXiris™ dialyzer, comprising a membrane based on a copolymer of acrylonitrile and sodium methallyl sulfonate, which has a homogeneous gel-structure and is coated with polyethyleneimine and heparin, also available from Gambro. According to a yet another embodiment of the invention, a membrane that can be used in the device of the present invention is a membrane also made from a copolymer of acrylonitrile and sodium methallyl sulfonate, which has a homogeneous gel-structure and is contained in filters sold under the trade name Filtral® (Gambro). According to yet another embodiment of the invention, the liver support system of the invention comprises, as dialyzer (1), the Nephral® ST dialyzer, comprising a membrane based on a copolymer of acrylonitrile and sodium methallyl sulfonate, also available from Gambro. According to still another embodiment of the invention, the liver support system of the invention comprises, as dialyzer (1), the Evodial® dialyzer, comprising a membrane based on a copolymer of acrylonitrile and sodium methallyl sulfonate, which has a homogeneous gel-structure and is coated with polyethyleneimine and heparin, also available from Gambro. According to still another embodiment of the invention, the liver support system of the invention may comprise, as dialyzer (1), dialyzers sold by Fresenius Medical Care as FX 80 and FX 100, both comprising the so-called Helixone® membrane, or the Optiflux® dialyzers F180NR or F200NR, dialyzers sold by Baxter Healthcare Corporation as Xenium XPH 210 or Xenium XPH 190, or dialyzers sold by Asahi Kasei Medical Co. as Rexeed-18S and Rexeed-21S.

The hollow fiber membrane dialyzer (2) which is used in a liver support system according to the invention is characterized in that it comprises a cylindrical filter housing, a bundle of essentially parallel hollow fiber membranes (3b) distributed longitudinally within the housing, a filtrate space (4b), which is closed off from the lumen space of the hollow fiber membranes (3b) and which is in fluid communication with an inlet means (7b) for feeding blood into the lumen space of the hollow fibers (3b) of the dialyzer and an outlet means (8b) for removing the treated blood from the lumen of the hollow fibers (3b), wherein the filtrate space (4b) of the dialyzer (2) is populated with particulate material (5), which comprises at least one adsorbent. The hollow fiber membrane of dialyzer (2) is characterized in that it is a so-called high cut-off membrane, which may generally be characterized by having a higher average pore size on the selective layer of the membrane than conventional membrane types, such as high-flux membranes, and, connected therewith, higher sieving coefficients for larger molecules. The mean pore size of a membrane gives an indication of the median or average size of the pores on a membrane surface. It may refer to the radius or the diameter. It also describes the particle size that the membranes will be able to reject or to let pass. Membrane pores tend to be rather non-uniform, and as such any assumption of shape and volume is mainly for the purpose of mathematical modeling and interpretation. However, the average pore size can give an accurate description and quantitative analysis of how a membrane will behave in certain situations. A high cut-off membrane in the context of the present invention refers to membranes which are defined by an average pore size on the selective layer of more than 7 nm, in general from between 8 to 12 nm, as determined according to the following equation [1] taken from Aimar et al. "A contribution to the translation of retention curves into pore size distributions for sieving membranes". *J. Membrane Sci.* 54 (1990) 339-354, $$\alpha = 0.33(MM)^{0.46} \qquad [1]$$

and based on dextran sieving coefficients determined as described, for example, in U.S. patent application Ser. No. 13/477,473, Example 3.

As used herein, the term "sieving coefficient (S)" refers to the physical property of a membrane to exclude or let pass molecules of a specific molecular weight. The sieving coefficient in whole blood, plasma or water can be determined according to standard ISO8 637, 2010. Put simply, the sieving coefficient of a membrane is determined by pumping a protein solution (e.g. bovine or human plasma) under defined conditions ($Q_B$, TMP and filtration rate) through a membrane bundle and determining the concentration of the protein in the feed, in the retentate and in the filtrate. If the concentration of the protein in the filtrate is zero, a sieving coefficient of 0% is obtained. If the concentration of the protein in the filtrate equals the concentration of the protein in the feed and the retentate, a sieving coefficient of 100% is obtained.

According to one aspect of the present invention, the membrane of the hollow fiber membrane dialyzer (2) is comprised of at least one hydrophobic polymer and at least one hydrophilic polymer. According to one embodiment of the invention, the hydrophobic polymer is chosen from the group consisting of polyarylethersulfone (PAES), polypropylene (PP), polysulfone (PSU), polycarbonate (PC), polyacrylonitrile (PAN), polyamide (PA) polytetrafluorethylene (PTFE) or combinations thereof, and the at least one hydrophilic polymer is chosen from the group consisting of polyvinylpyrrolidone (PVP), polyethyleneglycol (PEG), polyvinylalcohol (PVA), and copolymer of polypropyleneoxide and polyethyleneoxide (PPO-PEO). According to another embodiment of the invention, the membrane of the hollow fiber membrane dialyzers (2) is comprised of a hydrophobic polymer chosen from the group consisting of polyarylethersulfone (PAES) and polysulfone (PSU) and a hydrophilic polymer chosen from the group consisting of polyvinylpyrrolidone (PVP), polyethyleneglycol (PEG) and polyvinylalcohol (PVA). In yet another embodiment of the invention, the membrane of the hollow fiber membrane dialyzers (2) is comprised of a hydrophobic polymer chosen from the group consisting of polyarylethersulfone (PAES) and polysulfone (PSU) and the hydrophilic polymer polyvinylpyrrolidone (PVP).

According to another aspect of the present invention, the membrane of the hollow fiber membrane dialyzer (2) is characterized by a molecular weight cut-off in water, based on dextran sieving coefficients, of between 170 and 320 kD and a molecular weight retention onset in water, based on dextran sieving coefficients, of between 10 and 20 kD. According to another embodiment of the invention, the membrane has a molecular weight cut-off in water, based on dextran sieving coefficients, of between 90 and 200 kD. According to yet another embodiment of the invention, the membrane has a molecular weight cut-off in water, based on dextran sieving coefficients, of between 120 and 170 kD.

The hollow fiber membrane of dialyzer (2) allows a certain, sufficient amount of albumin to pass the membrane wall and get in contact with the particulate material (5) which populates the filtrate space (4b) of the dialyzer. The albumin, in the context of the present invention, may have bound thereto liver toxins which will be removed at least step-wise upon contact with the particulate material (5) in the filtrate space. It is obvious that other liver toxins may also pass the membrane wall and may be adsorbed by or bound to the particulate material (5). The cleansed permeate comprising the albumin with essentially no toxins bound thereto can leave the filtrate space by re-entering the lumen space of the hollow fiber membranes from where it can leave the dialyzer (2) through outlet means (8b). A given molecule, such as albumin, may of course pass the membrane wall more than once during its passage through dialyzer (2) and may thus have more than one opportunity to contact the particulate material (5) whereby bound toxins may be removed.

According to another embodiment of the invention, the membrane of the hollow fiber membrane dialyzer (2) is characterized in that it allows passage of substances having a molecular weight of up to 45 kD with a sieving coefficient measured in whole blood of between 0.1 and 1.0 according to ISO 8637. According to another embodiment of the invention, the membrane of the hollow fiber membrane dialyzer (2) has a sieving coefficient for albumin, measured in bovine blood plasma, of between 0.05 and 0.3 according to ISO 8637 with $Q_B$ max and UF 20%, 37° C., plasma protein content 60 g/l, and a sieving coefficient for albumin, measured in whole blood, of between 0.1 and 0.3 according to ISO 8637 at 37° C., protein level 60 g/l, $Q_B$ max and UF 20%.

The manufacturing of a membrane for preparing the hollow fiber membrane dialyzer (2) follows a phase inversion process, wherein a polymer or a mixture of polymers is dissolved in a solvent to form a polymer solution. The solution is degassed and filtered and is thereafter kept at an elevated temperature. Subsequently, the polymer solution is extruded through an outer ring slit of a nozzle having two concentric openings. Simultaneously, a center fluid is extruded through an inner opening of the nozzle. At the outlet of the spinning nozzle, the center fluid comes in contact with the polymer solution and at this time the precipitation is initialized. The precipitation process is an exchange of the solvent from the polymer solution with the non-solvent of the center fluid. By means of this exchange the polymer solution inverses its phase from the fluid into a solid phase. In the solid phase the pore structure, i.e. asymmetry and the pore size distribution, is generated by the kinetics of the solvent/non-solvent exchange. The process works at a certain temperature which influences the viscosity of the polymer solution. The temperature at the spinning nozzle and the temperature of the polymer solution and center fluid is 30 to 80° C. The viscosity determines the kinetics of the pore-forming process through the exchange of solvent with non-solvent. Subsequently, the membrane is preferably washed and dried. By the selection of precipitation conditions, e.g. center fluid composition, temperature and speed, the hydrophobic and hydrophilic polymers are "frozen" in such a way that a certain amount of hydrophilic end groups are located at the surface of the pores and create hydrophilic domains. The hydrophobic polymer builds other domains. A certain amount of hydrophilic domains at the pore surface area are needed to avoid adsorption of proteins. The size of the hydrophilic domains should preferably be within the range of 20 to 50 nm. In order to repel albumin from the membrane surface, the hydrophilic domains also need to be within a certain distance from each other. By the repulsion of albumin from the membrane surface, direct contact of albumin with the hydrophobic polymer, and consequently the absorption of albumin, are avoided. The polymer solution used for preparing the membrane preferably comprises 10 to 20 wt.-% of hydrophobic polymer and 2 to 11 wt.-% of hydrophilic polymer. The center fluid generally comprises 45 to 60 wt.-% of precipitation medium, chosen from water, glycerol and other alcohols, and 40 to 55 wt.-% of solvent. In other words, the center fluid does not comprise any hydrophilic polymer. In one embodiment, the polymer solution coming out through the outer slit openings is, on the outside of the precipitating fiber, exposed to a humid steam/air mixture. Preferably, the humid steam/air mixture has a temperature of at least 15° C., more preferably at least 30° C., and not more than 75° C., more preferably not more than 60° C. Preferably, the relative humidity in the humid steam/air mixture is between 60 and 100%. Furthermore, the humid steam in the outer atmosphere surrounding the polymer solution emerging through the outer slit openings preferably includes a solvent. The solvent content in the humid steam/air mixture is preferably between 0.5 and 5.0 wt-%, related to the water content. The effect of the solvent in the temperature-controlled steam atmosphere is to control the speed of precipitation of the fibers. When less solvent is employed, the outer surface will obtain a denser surface, and when more solvent is used, the outer surface will have a more open structure.

Before the extrusion, suitable additives may be added to the polymer solution. The additives are used to form a proper pore structure and optimize the membrane permeability, the hydraulic and diffusive permeability, and the sieving properties. In a preferred embodiment, the polymer solution contains 0.5 to 7.5 wt.-% of a suitable additive, preferably chosen from the group comprising water, glycerol and other alcohols. The solvent may be chosen from the group comprising N-methylpyrrolidone (NMP), dimethyl acetamide (DMAC), dimethyl sulfoxide (DMSO) dimethyl formamide (DMF), butyrolactone and mixtures of said solvents. Methods for producing suitable membranes are disclosed, for example, in WO 2004/056460 A1 or in U.S. patent application Ser. No. 13/477,473.

According to one embodiment of the invention, hollow fiber membranes which can be used for preparing a hollow fiber membrane dialyzer (2) according to the invention are membranes which are known in the art and are currently used in dialyzers commercially available under the trade names HCO1100® or Theralite® from Gambro Lundia AB. For example, the Theralite® membrane is prepared from polyethersulfone and PVP and has a wall thickness of 50 µm and an inner diameter of 215 µm. With bovine plasma having a protein level of 60 g/l (albumin level 20-30 g/l) at 37° C. and at $Q_B$=250 ml/min, $Q_D$=500 ml/min and UF=0 ml/min, the albumin loss during the first 4 hours is about up to 28 g, and after 4 hours the average albumin loss per hour (±20%) is about 7 g for a membrane as used in the Theralite® dialyzer.

According to another embodiment of the invention, the fiber packing density or fiber allocation within the dialyzer (2) is in the range of from 20% to 50%. According to yet another embodiment of the invention, the total membrane area of the dialyzer (2) is in the range of between 1.0 and 2.1 m². The fibers in the dialyzer preferably are homogenously distributed over the length of the cylindrical housing of the filter module, which means that the distance between the single fibers remains essentially the same over the total length of the fibers. In another embodiment of the invention, the fiber allocation is between 25% and 55%. In yet another embodiment of the invention, the fiber allocation is between 25% and 45%.

The fibers which can be used for producing a module according to the invention can be straight or crimped, wherein crimped fibers are fibers having a certain ondulation which is essentially sinusoidal but may deviate from such sinusoidal ondulation over the length of the fiber, i.e. wavelength and/or amplitude of the crimps of one single fiber or between two or more fibers may be different. Ondulated fibers and methods for ondulating fibers are known in the art and have been described, for example, in EP 1 257 333 A1. It is possible to combine straight and crimped fibers in one device. In one embodiment of the invention, all of the fibers in the filter module are ondulated. According to another embodiment of the invention, all of the fibers in the filter module are straight fibers. For a hollow fiber membrane dialyzer (2) according to the invention, it may be advantageous to use ondulated fibers with an amplitude of between 0.1 mm and 0.9 mm and a wavelength of between 3.5 mm and 11.5 mm. For example, the standard hollow fiber which is used in a Theralite® dialyzer has an amplitude of 0.6 mm and a wavelength of about 7.3 mm.

According to another embodiment of the invention, the membrane surface area of a hollow fiber membrane dialyzer (2) is in the range of from 1.0 to 2.1 m². Generally, a membrane surface area of between 1.3 and 1.8 m² will be sufficient for allowing an effective removal of liver toxins with dialyzer (2) according to the invention. According to yet another embodiment of the invention, the fiber dimensions are in the range of 180-250 µm (inner diameter) and 35-80 µm (wall thickness).

According to one aspect of the invention, the hollow fiber membrane dialyzer (2) according to the invention comprises a bundle of microporous hollow fiber membranes as described before and further comprises, in the filtrate space of the module, a particulate material (5) which populates the filtrate space of the hollow fiber membrane dialyzer (2), wherein the particulate material (5) is able to immobilize or adsorb liver toxins which have passed the hollow fiber membrane. The particulate material may consist of hydrophobic and/or hydrophilic material and is chosen from the group consisting of oxygen-containing adsorbents, carbon-based adsorbents and polymer-based adsorbents or combinations thereof. The expression "adsorption" as it is used herein refers to the preferential partitioning of substances from liquid phase onto the surface of a solid substrate (the particulate material). Physical adsorption is caused mainly by van der Waals forces and electrostatic forces between adsorbate molecules and the atoms which compose the adsorbent surface. Thus adsorbents are characterized first by surface properties such as surface area and polarity. Non-polar adsorbents are generally referred to a as "hydrophobic". Carbonaceous adsorbents, polymer adsorbents and silicalite are typical non-polar adsorbents.

The expression "particulate material" as used herein refers to the material which is filled into and populates the filtrate space of a hollow fiber membrane module or filter. The particulate material is generally referred to, throughout the description, as consisting of particles having a certain average diameter. Said particles, for the sake of simplicity, are deemed to have a convex shape, the diameter of which is defined to be the largest distance that can be formed between two opposite parallel lines tangent to its boundary, and the width is defined to be the smallest such distance. In general the particles are assumed to be essentially spherical in nature, meaning that diameter and width are the same. According to another embodiment of the invention, the particulate material consists of particles having a diameter of between 1 µm to 300 µm.

According to yet another embodiment of the invention, the filtrate space is homogenously populated with a particulate material with a certain filling ratio which is adapted to the particulate material used, the packing density within the housing and the geometry of the housing itself, comprising the available volume of the filtrate space. The expression "homogenous" as used herein means that the particulate material, i.e. the particles it consists of, is evenly distributed over the filtrate space. This means that the average number of particles per volume, for example cm³, is essentially the same over the space. The expression "essentially the same" used in connection with the average number of particles in a cm³ means that the number of particles in a given volume area of 1 cm³ may differ from the number of particles in a second volume area of 1 cm³ by not more than up to 20%, preferably by not more than 10%.

The expression "filling ratio" as used herein, refers to the ratio of the volume in ml of the maximal amount of particulate material, in its dry form or wet form, respectively, which can be accommodated in the filtrate space of a given hollow fiber membrane module ($V_{PM}$) and the utilizable volume in ml of the filtrate space of said module ($V_{FS}$):

$$\text{Filling ratio} = \frac{V_{PM}(\text{ml})}{V_{FS}(\text{ml})}.$$

$V_{PM}$ (ml) thus represents the volume of the particulate material which can be accommodated in the filtrate space of the device. $V_{FS}$ (ml) represents the utilizable filtrate space, which is known or can easily be determined for a given hollow fiber membrane filter module. A ratio of 1.0 would thus mean that the complete utilizable volume of the filtrate space is occupied by the particulate material. The lower the ratio gets, the less particulate material is present in the filtrate space of the module. The filling ratio always refers to modules wherein essentially the complete utilizable volume of the module has been exhausted. "Exhausted", in the context of the present invention, means that no more particulate material can be filled into the device. $V_{PM}$ (ml) can be calculated from the total amount of particulate material in g which can been filled into the module with a given method, divided by the bulk density (g/ml) of the material. The bulk density of a particulate material is defined as the mass of the particles of the material per total volume they occupy. It should be noted that the bulk density of a particulate material can change depending on how the material is treated. For example, the particulate material, simply poured into a cylinder, will have a certain bulk density ("bulk density"). If the cylinder is agitated, the particles will move and usually settle closer together, resulting in a higher bulk density. For this reason, the bulk density of the particulate material in a filter which was prepared according to the invention is referred to as a "tapped density" (ρ), which in principle refers to the bulk density of the particulate material after compaction. For a given material ρ can be determined according to DIN ISO 3953. The maximal bulk density ("tapped density") is reached when no further compaction of the material takes place. The volume $V_{PM}$ (ml) of the particulate material which can be accommodated in the filtrate space of a given hollow fiber membrane module can thus be calculated:

$$V_{PM}(\text{ml}) = \frac{m_{PM}(\text{g})}{\rho(\text{g/ml})}.$$

$m_{PM}$ represents the amount of particulate material which could be accommodated in the filtrate space of the module. $m_{PM}$ can be determined for example by subtracting the amount of remaining particulate material (filtered off and dried, in case the material was filled into the module as a suspension) from the initial quantity of (dry) particulate material. According to one aspect of the present invention, dialyzer (2) provides for filling ratios in a range of between 0.6 and 1.0. According to another aspect of the invention, dialyzer (2) provides for filling ratios in a range of between 0.4 and 0.7. According to yet another aspect of the invention, dialyzer (2) provides for filling ratios in a range of between 0.3 and 0.5.

The uncharged or non-polar hydrophobic material for binding and/or adsorbing liver toxins which populates the filtrate space of the hollow fiber membrane dialyzer (2) according to the invention may be chosen from a range of materials which are generally known in the art. According to one aspect of the present invention hydrophobic particulate material is chosen from the group consisting of activated carbon, carbon nanotubes, hydrophobic silica, styrenic polymers, polydivinylbenzene polymers and styrene-divinylbenzene copolymers. Activated carbon can be used, for example, in particulate form as powder or fine granules less than 1.0 mm in size with an average diameter between 0.001 and 0.15 mm or as granular activated carbon with relatively larger particle size compared to powdered activated carbon. Granular activated carbon has the advantage of easier handling and higher safety with regard to its retention in the filtrate space. Activated carbon which may be used in dialyzer (2) according to the invention may be acid washed granular activated carbon particles. According to one aspect of the present invention, the particle size of the granular activated carbon is in the range of from >10 mesh (2.0 mm) and <40 mesh (0.420 mm). According to another aspect of the present invention, particle size of the activated carbon is in the range of about 0.200 mm. The total surface area of activated carbon which may be advantageously used according to the invention is in the range of from 600 $m^2/g$ and 1200 $m^2/g$. Such activated carbon can be purchased, for example, as Norit® GAC 1240 PLUS A (Norit Nederland BV). Examples for polymeric hydrophobic material which can be used, are, for example, styrenic polymers like DOWEX™ OPTIPORE™ L493 and V493 or Amberlite® XAD®-2, polydivinylbenzene polymers or styrene-divinylbenzene copolymers (e.g. Amberlite® XAD4 or Amberchrom™ CG161), poly(1-phenylethene-1,2-diyl) (Thermocole), or hydrophobic silica, which is silica that has hydrophobic groups chemically bonded to the surface, or combinations thereof. Hydrophobic silica can be made both from fumed and precipitated silica. Another hydrophobic material which can be used is known as Ujotit, a copolymer of styrene and divinylbenzene without any functional groups, which is available as Ujotit PA-30, Ujotit PA-40 or Ujotit PA-20. According to one embodiment of the present invention, the particulate material in the filtrate space of dialyzer (2) comprises a copolymer of styrene and divinylbenzene without any functional groups, such as Ujotit PA-30. Ujotit PA-30 particles or beads have an average diameter of between 80-200 μm and a specific surface of between 750-850 $m^2/g$. According to another embodiment of the present invention, the particulate material in the filtrate space of dialyzer (2) comprises activated carbon, such as, for example, Norit® GAC 1240 PLUS A (Norit Nederland BV). According to yet another embodiment of the invention, the particulate material in the filtrate space of dialyzer (2) comprises, as uncharged hydrophobic material, a combination of at least one activated carbon and at least one copolymer of styrene and divinylbenzene without any functional groups.

The charged or polar hydrophilic material for binding and/or adsorbing liver toxins which populates the filtrate space of the hollow fiber membrane dialyzer (2) according to the invention may be chosen from a range of materials which are known in the art. According to another aspect of the present invention, the particulate material may consist of cation exchange particles which may be used without further modification. Such cation exchange material is generally based on matrices of agarose, cellulose, dextran, methacrylate, polystyrene or polyacrylic acid. Such materials are generally known and commercially available, for example, under trade names such as Sepharose® CM, Sephadex, Toyopearl®, Amberlite®, Diaion™, Purolite®, Dowex® and Duolite® $SO_3H$, respectively.

According to another aspect of the present invention, the particulate material may consist of anion exchange material which can be used without further modification. Such anion exchange material may be based on polystyrene or styrene-divinylbenzene and which may be unmodified or modified with sulphonic acids, polyamines or quaternary or tertiary amines. According to one aspect of the invention, the particles are based on a copolymer of styrene and divinylbenzene carrying active groups such as quaternary ammonium groups, dimethylethanolamine groups, dimethylethanolbenzyl ammonium groups, benzyltrialkyl ammonium groups, benzyldimethyl(2-hydroxyethyl)ammonium and/or trimethylbenzyl ammonium functional groups. According to a specific aspect of the present invention, the particles used are based on a copolymer of styrene and divinylbenzene carrying quaternary ammonium groups. According to one aspect of the invention, the copolymer of styrene and divinylbenzene carries trimethylbenzyl ammonium functional groups, which is also referred to as Cholestyramine, Cuemid, MK-135, Cholbar, Cholbar, Questran, Quantalan, Colestyramine or Dowex® 1x2-Cl. Such anion exchange media which can be used are known, for example, under the trade name Amberlite®. Amberlite® comprises, for example, a matrix formed of styrene-divinylbenzene having active or functional groups such as quaternary ammonium groups, benzyldimethyl(2-hydroxyethyl)ammonium groups or dimethylethanolamine groups. Other anion exchange media which can be used are known, for example, under the trade name Dowex®. Dowex® comprises, for example, a matrix formed of styrene-divinylbenzene which may have active or functional groups such as trimethylbenzylammonium. According to one embodiment of the invention, the particulate material in the filtrate space of dialyzer (2) comprises at least one copolymer of styrene and divinylbenzene carrying trimethylbenzyl ammonium functional groups, such as, for example, Cholestyramine, Cuemid, MK-135, Cholbar, Cholbar, Questran, Quantalan, Colestyramine, Purolite® or Dowex® 1x2-Cl.

According to yet another embodiment of the invention, the particulate material in the filtrate space of dialyzer (2) comprises a combination of at least one activated carbon, at least one copolymer of styrene and divinylbenzene without any functional groups and at least one copolymer of styrene and divinylbenzene carrying trimethylbenzyl ammonium functional groups. Possible ratios between the respective components are in the range of from 1:1:1 and 10:5:1. According to still another embodiment of the invention, the particulate material in the filtrate space of dialyzer (2) comprises a combination of at least one copolymer of styrene and divinylbenzene without any functional groups and at least one copolymer of styrene and divinylbenzene carrying trimethylbenzyl ammonium functional groups. Possible ratios between the respective components are in the range of from 10:1 to 1:1.

According to one embodiment of the invention, the polymeric particulate material is used in the form of beads, which are small, essentially spherical particles which may differ in size and composition and can have an average diameter in the range of from 100 nm to 5 mm and especially in the range of from 3 μm to 300 μm.

For preparing a hollow fiber membrane dialyzer (2) according to the invention, the particulate material is preferably introduced into the filtrate space in a way which allows a homogeneous distribution of the particulate material (5) within the filtrate space (4b). The particulate material (5) can be filled into the filtrate space in a dry form, wherein the material is filled in from top to bottom through inlet port (10b). In this case, the filter module should have an inclined position. The particulate material may also be filled into the filtrate space as a suspension, for example, in water. The dry particulate material or the suspension of the material may also be introduced into the filtrate space from top to bottom through inlet port (10b). In the alternative, the suspension may be introduced into the filtrate space from bottom to top through outlet port (11b), wherein the filter module is held in a vertical or inclined, preferably in a vertical position. In the context of the present invention, the expressions "inlet port" and "outlet port" are assigned to certain ports such as (10b) and (11b) irrespective of their actual use for introducing or removing material into or out of the filtrate space. For example, an "outlet port" like outlet port (11b) may in principle be used to remove fluid from the filtrate space from the device and thus serve as an "outlet", but may also be used to introduce material into the device, thus serving as an "inlet". However, in order to avoid double assignments, the respective ports have been named either "inlet" or "outlet" ports without wanting to restrict the ports to a certain use.

The module according to the invention should be prepared in a way that the filtrate space is homogenously populated with the hydrophobic material. At the same time a high filling ratio is advantageous in order to improve the capacity of the device. Accordingly, a high filling ratio of between 0.6 and 1.0 is desirable, even though lower filling ratios may also be sufficient to achieve very good results. Lower ratios may then be preferred. Like that, the modules are designed to provide an optimized permeation of flow so that once the substances present in the fluid to be treated, comprising the target liver toxins, enter the filtrate space of the module they are evenly distributed throughout the active particulate material and will be adsorbed or bound and thus removed with high efficiency. As described before, the filling process may be accomplished, for example, with a filling device which is designed to allow positioning the module at a certain angle of inclination, preferably between 45° and 90° C. with regard to its longitudinal axis. Such filling device (FIGS. 4A and 4B) can be designed to optimize the filling process by alternately rotating the hollow fiber filter module clockwise and counter-clockwise around its longitudinal axis in quick succession with a minimum total angular displacement (θ) of about 10°. The rotational movement of the module during filling the filtrate space, optionally in combination with a certain angle of inclination for dry material, allows for an improved distribution and deposition of the particulate material between the hollow fibers over the complete utilizable space of the housing. Preferably, the module during the process of filling is additionally exposed to a force which is applied perpendicular to the longitudinal axis of the module with the help of a rapping means. Such pushing or rapping impact on the filter module during filling further improves the homogenous distribution and deposition of the particulate material in the filtrate space. The pushing or rapping force can be achieved, for example, by complementing the filling device as shown in FIGS. 4A and B with a pneumatic interval impactor. It further increases the total amount of particulate material which can be homogenously deposited in the filtrate space of the module. According to one embodiment of the invention, the filling process is accomplished by filling the particulate material into the filtrate space in its wet form (FIG. 4B). A detailed description of the filling process which can be applied for preparing a module according to the invention is described in European Patent Application entitled "Filter device combining beads and fibers" which was filed by the applicant on the same day as the present application and which is incorporated herein by reference. However, any means or process can be used for introducing the hydrophobic particles into the filtrate space, as long as the particles are distributed within the filtrate space in way that enables the presence and homogeneous distribution of enough material to allow for the efficient removal of the target liver toxins from the fluid to be treated.

Various kinds of housings can be used for preparing a module according to the invention, comprising those known in the art as housings for hemodialyzers, hemodiafilters or plasmafilters. Dialysis filter housings can be produced from a variety of plastic materials by a variety of processes, such as injection molding. For example, polycarbonates and polypropylenes are widely used in a variety of molding and extrusion applications and can also be used for the module disclosed here. For example, it is possible to use a housing which is otherwise used for a standard dialysis filter, such as, for example, the Polyflux®210H housing. However, it is apparent that other housings having different dimensions can be used without deviating from the spirit of the present invention.

According to one aspect of the invention, the hollow fiber membrane dialyzer (2) is part of an extracorporeal liver support system or device for the removal of liver toxins, including albumin bound liver toxins, from blood. Such liver support systems are used for treating conditions of liver failure. The treatment preferably consists in the elimination of liver toxins comprising protein-bound toxins from the patient's blood. In the context of the present invention, substances which, in the course of liver failure, have been shown to specifically accumulate and/or negatively affect the patient and which need to be removed by a liver support system are referred to as "liver toxins". Liver toxins in the sense of the present description thus comprise, without limitation, ammonia, mercaptans, phenols, bilirubin, bile acids (e.g. chenodeoxycholic acid), certain vasodilators (e.g. aldosterone, norepinephrine, vasopression, plasma renin), metabolites of aromatic amino acids, lactic acid, urea, uric acid, medium-chain fatty acids and pro- and anti-inflammatory cytokines (e.g. IL6, IL8, IL10, TNFa, sTNFaR1), leukemia inhibitory factor (LIF), liver cell growth inhibitors such as TGF-ß1 and drugs that may cause liver damage or failure (e.g. diazepam, acetaminophen, phenylbutazone). For example, hydrophobic bile acids are cytotoxic at high concentrations and their accumulation within hepatocytes may lead to apoptosis or necrosis. Pro-inflammatory cytokines are believed to mediate hepatic inflammation, apoptosis and necrosis of liver cells, cholestasis, and fibrosis (see, for example, Stauber et al (2010): MARS and Prometheus in Acute-on-Chronic Liver Failure: Toxin Elimination and Outcome. *Transplantationsmedizin* 22:333-338). The treatment of a patient suffering from liver failure, with a liver support device according to the invention, results in a reduced blood level of such liver toxins. It should be noted here that such toxins as are generally removed during standard renal hemodialysis, and which could also be referred to as "renal" or "uremic" toxins (urea etc.) will also be removed by the liver support system by hollow fiber membrane dialyzer (1). In the context of the present invention, the expression "liver toxins" generally encompasses such uremic toxins.

The term "liver failure" in the context of the present invention refers to the inability of the liver to perform its normal synthetic and metabolic function as part of normal physiology. Liver failure thus leads, for example, to an insufficient detoxification of albumin, which is followed by an exhaustion of the binding capacity of albumin and an enrichment of the otherwise albumin-bound toxins, e.g. of unconjugated bilirubin. Treatment is indicated, for example, at a bilirubin concentration of >10 mg/dL. However, there are liver disorders where a liver dialysis treatment is indicated, but which is not characterized by increased bilirubin levels. Disorders which are associated with the expression "liver failure" as used in the present invention include, but are not limited to, hepatorenal syndrome, decompensated chronic liver disease, acute liver failure, graft dysfunction after liver transplantation, liver failure after liver surgery, secondary liver failure, multi organ failure, exogenous intoxication or intractable pruritus in cholestasis etc.

Liver dialysis according to the invention may be carried out (FIG. 3) by passing the patient's (12) blood into a first dialyzer (1). Dialyzer (1) is perfused with the patient's blood (6) which enters the dialyzer at inlet port (7a), and a dialysate solution (9) which enters dialyzer (1) at inlet port (10a) is passed in a continuous flow through the filtrate space (4a) in a direction opposite to the blood flow within the hollow fibers (3a). Dialyzer (1) is thought to effectively remove smaller molecules which may be referred to as uremic toxins as they are removed also in renal hemodialysis treatments provided to patients with renal impairment. Consequently, dialyzer (1) does not allow passage of an essential amount of albumin over the membrane wall. The treated blood leaves dialyzer (1) at outlet port (8a) and enters dialyzer (2) through inlet port (7b). The second hollow fiber membrane dialyzer (2) which allows the passage of essential amounts of albumin over the membrane wall and which receives the blood (6) of the first dialyzer (1) through inlet port (7b) has a filtrate space (4b) which is closed off from the lumen space of the hollow fiber membranes (3b). The filtrate space is not perfused by any dialysis solution but is populated with a particulate material (5) which is constituted of one or several materials which are able to bind or adsorb liver toxins.

It is another advantage of the present liver support system that no additional or specifically adapted dialysis machine is needed for performing the treatment according to the invention. Dialysis machines which are currently used for hemodialysis treatments of patients suffering from chronic or acute renal diseases can also be used for the current liver support system. Examples for dialysis monitors which can be used are, for example, the PrismafleX® or Artis™ dialysis machines, both of Gambro, or the 2008, 4008 and the 5008 dialysis machine series of Fresenius Medical Care. Generally, the liver support system according to the invention can be run in standard CRRT modes, such as CVVHD or CVVHDF.

Flow rates used in liver support systems according to the invention may vary over a certain range and are known to persons with skill in the art. Standard flow rates are, for example, a $Q_B$ (blood flow) of 100-500 ml/min, preferably 150-250 ml/min, a $Q_D$ for IC units (e.g. Prismaflex®) of 100-800 ml/min and a $Q_D$ for standard chronic dialysis units of 300-800 ml/min. The treatment time may vary for a given patient. However, treatment times are usually in the range of from 8 to 10 hours.

It is known that albumin can be adsorbed, to a certain extent, to the adsorbent which is present in the filtrate space of dialyzer (2). Albumin is synthesized only in the liver. The albumin concentration in plasma in healthy humans usually ranges between 33 and 52 g/l. The normal rate of albumin synthesis is about 0.2 g per kg body weight per day and a steady state exists between albumin synthesis and metabolism. The amount of albumin metabolized daily is believed to be proportional to the plasma concentration, meaning that a fixed percentage of about 10% of plasma albumin content is metabolized per day. The half-life of albumin is inversely proportional to the plasma albumin concentration, that is, a decreased albumin content results in increased half-life, whereas increasing albumin concentrations cause the metabolic rate to increase by up to 50% (Boldt, Br. J. Anaesth. (2010) 104 (3): 276-284). Therefore, a substitution of the albumin which may be adsorbed by the adsorbent during the treatment with a liver support system according to the invention may not be necessary. However, substitution of albumin may be indicated especially in cases of spontaneous bacterial peritonitis (SBP), hepatorenal syndrome (HRS), and post-paracentesis syndrome (PPS) due to the fact that the liver is severely compromised. Substitution can be done according to the state of the art, mostly by infusion. Therefore, according to one aspect of the invention, liver support or dialysis treatment according to the invention may be followed by the substitution of albumin which was adsorbed during the treatment in order to maintain a serum albumin level of above 30 g/l.

It will be readily apparent to one skilled in the art that various substitutions and modifications may be made to the invention disclosed herein without departing from the scope and spirit of the invention. The present invention will now be illustrated by way of non-limiting examples of preferred embodiments in order to further facilitate the understanding of the invention.

EXAMPLES

Example 1

Preparation of a Hollow Fiber Membrane for Use in Dialyzer Module (2)

Two solutions are used for the formation of the membrane, the polymer solution consisting of hydrophobic and hydrophilic polymer components (21 wt-%) dissolved in N-methyl-pyrrolidone, and the center solution being a mixture of N-methyl-pyrrolidone and water. The polymer solution contains polyethersulfone (PES 14.0 wt-%) and polyvinylpyrrolidone (PVP 7.0 wt-%) as membrane building components. The solution further contains NMP (77.0 wt-%) and water (2.0 wt-%). The center solution contains water (53.0 wt-%) and NMP (47.0 wt-%). During the membrane formation process polymer and center solution are brought in contact with a spinneret or jet and the membrane precipitates. A defined and constant temperature (58° C.) of the spinneret, the polymer solution and the center solution is used to support the process. The precipitated hollow fiber falls through a humidified shaft filled with steam (100% relative humidity, 54° C.) into a coagulation/washing bath (20° C., ~4 wt-% NMP). The membrane is further washed in two additional water baths (70° C.-90° C.) with counter current flow (250 l/h). Membrane drying is performed online, wherein remaining water is removed, and after formation of a fiber bundle the bundle is potted into a housing.

Example 2

Preparation of a Hollow Fiber Membrane Dialyzer (2) Comprising Hollow Fibers and Particulate Material in the Filtrate Space (Suspension Filling)

Standard hollow fibers prepared according to Example 1 were used to prepare filter modules with active particulate material on the filtrate side of the module. The housings used possess connectors at the blood side and the filtrate side according to ISO 8637:2004. The fibers had an inner diameter of 215 μm and a wall thickness of 50 μm. The fibers were slightly crimped with a depth of 0.6 mm or 0.8 as shown in Table I. The total membrane surface area was either 1.9 m² or 1.7 m² as shown in Table I. The housings had a diameter of 48 mm and a total length (effective fiber length) of 270 mm. The potting material consisted of polyurethane.

TABLE I

| Prototypes | 2 | 3 | 4 | 5 | 6 | 7 | 9 |
|---|---|---|---|---|---|---|---|
| Membrane area A [m²] | 1.9 | 1.9 | 1.9 | 1.9 | 1.7 | 1.7 | 1.9 |
| Ujotit PA-30 [g] | 46.92 | 39.17 | 43.69 | 35.63 | 60.42 | 42.47 | 34.39 |
| Cholestyramine [g] | 5.21 | 13.06 | 6.72 | 17.82 | 20.14 | 21.24 | 17.20 |
| Active carbon [g] | 0 | 0 | 16.81 | 17.82 | 0 | 21.24 | 17.20 |
| Total amount particulate material [g] | 52.13 | 52.23 | 67.22 | 71.27 | 80.56 | 84.95 | 68.79 |
| Ondulation depth [mm] | 0.6 | 0.6 | 0.6 | 0.6 | 0.6 | 0.6 | 0.8 |

Figure 4:
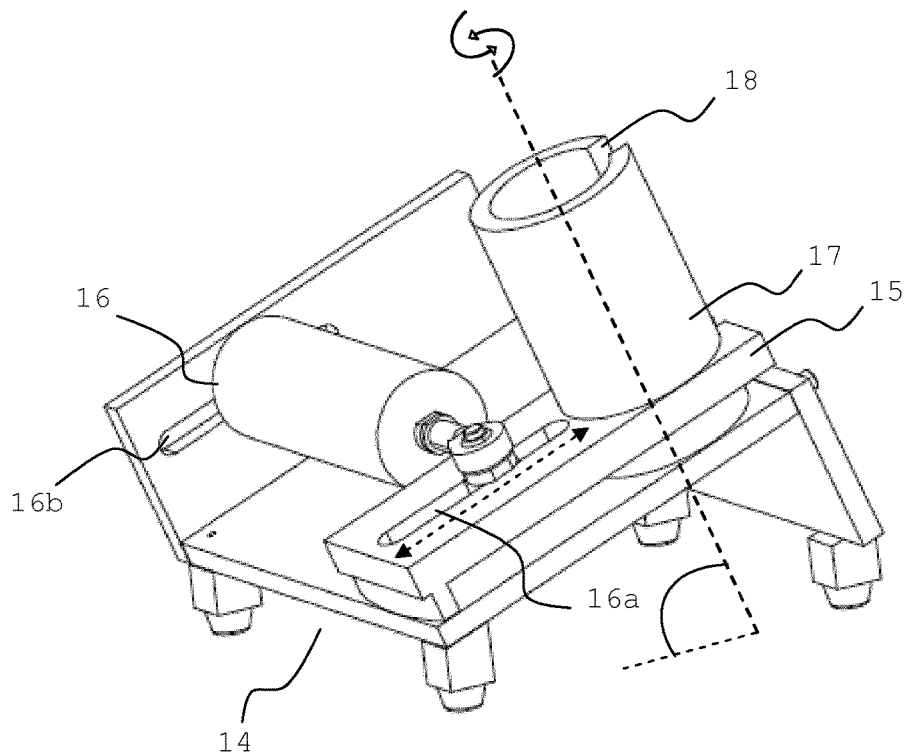
FIG. 4 shows a filling device (14) which may be used to fill in the adsorbent material into a hollow fiber membrane dialyzer (2) according to the invention. The dialyzer can be positioned in the mounting (17) of the device, which may have a slot (18) for accommodating outlet port (11b) and optionally also inlet port (10b) of the filter module. The mounting (17) is fixed to swiveling unit (15), which is in communication with a pneumatic linear vibrator (16). The vibrator (16) can be moved back and forth within slots (16a) and (16b), thereby adjusting the angular displacement of the swiveling unit (15) and the mounting (17). The swiveling unit (15) together with the mounting (17) are designed as a movable element which can be moved back and forth around essentially the longitudinal axis of the module. The filling device (14) may be designed to allow an upright positioning (90°) of the filter module during filling (FIG. 5B) or an inclination of the filter module (FIG. 5A), depending on the filling process (dry or suspension) and the characteristics of the adsorbent.
Figure 4:
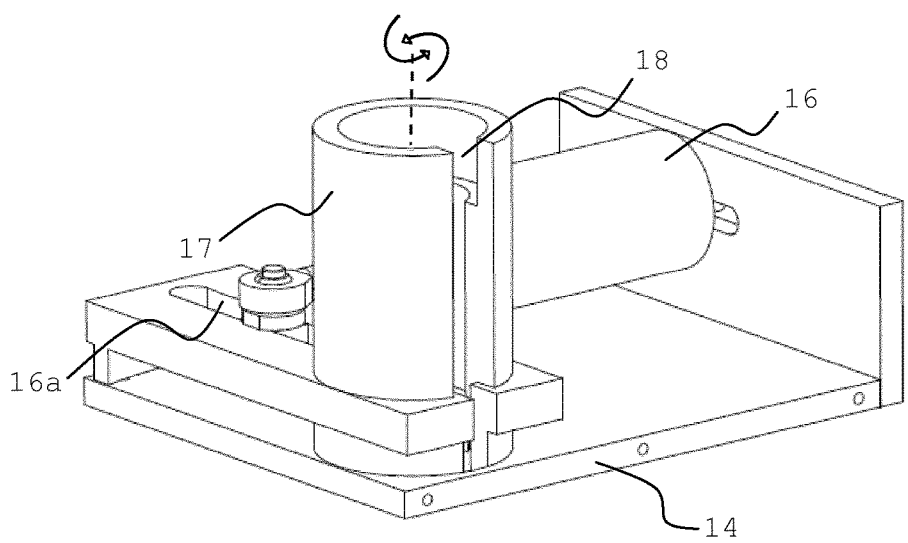

Seven filters were filled with particulate material as shown in Table I in accordance with the filling set-up as shown in FIG. 4 and as indicated in Table II. The particulate material used was Ujotit PA-30 particles, having an average diameter of between 80-200 μm and a specific surface of between 750-850 m²/g (Dr. Felgenträdger & Co.—Ökochem. and Pharma GmbH, Dessau-Roßlau, Germany), cholestyramin (Purolite® A430MR from Purolite GmbH, Ratingen, Germany) and activated carbon (Norit® GAC 1240 PLUS A, Norit Nederland BV, The Netherlands).

TABLE II(A)

| Prototype No. | filter [g] | Ujotit PA30/ 200 (dry) [%] | Cholestyramin (dry) [%] | activated carbon (dry) [%] | Suspension volume [L] |
|---|---|---|---|---|---|
| 2 | 241.58 | 90 | 10 | 0 | 4.8 |
| 3 | 239.93 | 75 | 25 | 0 | 5 |
| 4 | 239.65 | 65 | 10 | 25 | 5 |
| 5 | 240.09 | 50 | 25 | 25 | 5 |
| 6 | 268.69 | 75 | 25 | 0 | 5 |
| 7 | 271.02 | 50 | 25 | 25 | 5 |
| 9 | 282.36 | 50 | 25 | 25 | 5 |

TABLE II(B)

| Prototype No. | Total amount particulate material | p (pneumatic linear vibrator) [bar] | p (pneumatic interval impactor) [bar] | Method (suspension) |
|---|---|---|---|---|
| 2 | 52.13 | 5.5 | 4.,5 (42 beats per min) | top to bottom |
| 3 | 52.23 | 5.5 | 4.,5 (42 beats per min) | bottom to top |
| 4 | 67.22 | 5.5 | 4.,5 (42 beats per min) | bottom to top (no inclination) |
| 5 | 71.27 | 5.5 | 4.,5 (42 beats per min) | bottom to top (no inclination) |
| 6 | 80.56 | 6.5 | 4.,5 (42 beats per min) | bottom to top (no inclination) |
| 7 | 84.69 | 6.5 | 4.5 (42 beats per min) | bottom to top (no inclination) |
| 9 | 68.79 | 6.5 | 4.5 (42 beats per min) | bottom to top (no inclination) |

Figure 5:
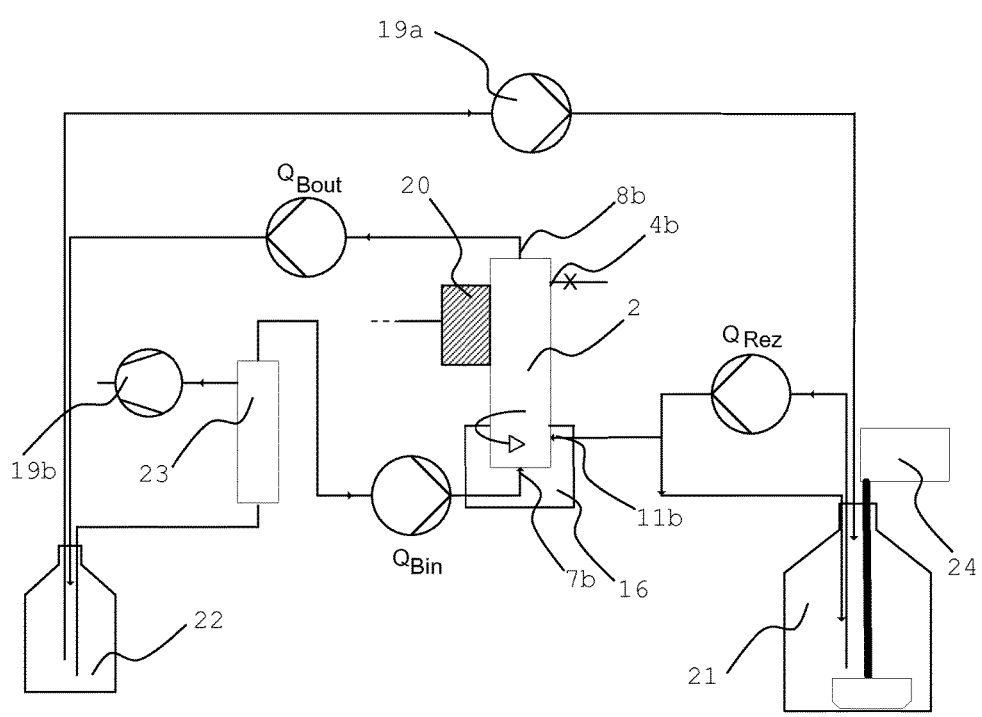
FIG. 5 shows a schematic representation of the process for the suspension filling of a filter module with particulate material, wherein the filter (2) is held in an upright (90°) position and the suspension of the particulate material is introduced into the filtrate space via outlet port (11b). An impactor (20) and vibrator (16) are enabled. The suspension is pumped in ($Q_{Rez}$) from a feed tank (21) which is equipped with a stirrer (24). The solvent leaves the module at inlet port (8b) after having passed the membrane wall, whereas the particulate material remains within the filtrate space, and the solvent is pumped ($Q_{Bout}$) into receiving tank (22). The solvent may be pumped back ($Q_{Bin}$) into the module via inlet port (7b) in order to assist in the filling process, wherein a deaeration unit (23), which is in communication with vacuum pump (19b), is used to avoid the introduction of air bubbles. Inlet port (10b) is closed.

The filters were weighed to identify the initial mass of the filters. The filters were then installed in the mounting (18) of the filling device (14) and a pneumatic interval impactor (Netter Druckluft-Intervallklopfer PKL 190, Netter GmbH, Germany) was attached to the filter module (FIG. 5). The mounting (18) was set to an inclination of 70°, where applicable. Outlet ports (10b) and (11b) was closed and inlet port (7b) was opened. Outlet port (8b) was also opened. A pneumatic linear vibrator (Netter Druckluft-Kolbenvibrator NTK 15x, Netter GmbH, Germany) was connected to the system and set to 5.5 bar. In a first step, the filters were filled on the blood side and the filtrate side with degassed RO water under avoidance of air bubbles. The pneumatic interval impactor as well as the pneumatic linear vibrator was connected to compressed air and the pumps were started with a flow rate of 100 ml/min. The beads were fed into the filtrate space at the bottom of the device and quickly settled at the top of it, followed by the gradual filling of the module with beads from the top until the filtrate space was completely filled. The process was stopped once the filtrate space was completely filled and pressure in the system increased and the unused beads remaining in the feed tank were dried and weighed. The results showing the total amount of particulate material which was introduced into the filtrate space can be taken from Table I. The tapped densities of materials shown in Table I (Ujotit PA-30; cholestyramine; active carbon) can be used to calculate the filling ratio for the modules according to DIN ISO 3953.

Example 3

Removal of Liver Toxins

Figure 1:
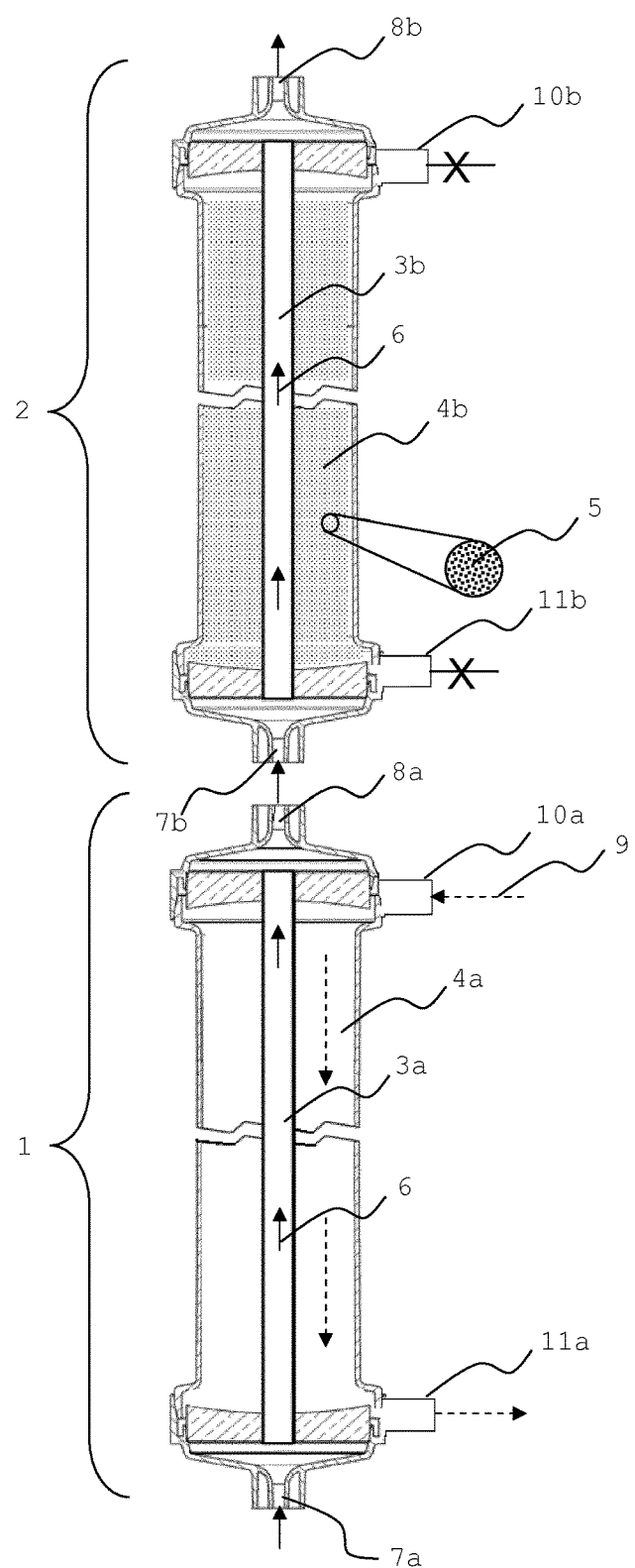
FIG. 1 shows a schematic representation of the essential portion of the liver support system of the invention, wherein (2) denotes the hollow fiber membrane dialyzer which comprises a hollow fiber membrane (3b) which allows for the passage of essential but limited amounts of albumin into the filtrate space (4b) which is populated with one or more adsorbents (5). For reasons of clarity, only one fiber is schematically shown in the Figure. The filtrate space is closed off from the lumen space of the hollow fibers. The blood (6), depicted as a solid line arrow, which enters the dialyzer at inlet (7b) is the retentate of a first standard hemodialyzer (1), which comprises a standard high-flux hemodialysis membrane for the removal of smaller molecular weight compounds and which is accordingly perfused with a dialysis solution (9), depicted as a dashed arrow, which enters the filtrate space through inlet (10a) and flows in a direction opposite to the flow direction of the blood within the lumen space of the hollow fibers (3a) before it leaves the dialyzer at outlet port (11a). The treated blood leaves the dialyzer (1) at outlet (8a) and subsequently enters dialyzer (2). Albumin and smaller compounds, comprising albumin-bound and water-soluble liver toxins which are to be captured by the adsorbent on the filtrate side are allowed to pass the membrane of dialyzer (2). The cleansed permeate may re-enter the lumen side of the hollow fiber membranes and leave the device together with the blood through outlet (8b). Optional inlet (10b) and optional outlet (11b) are closed in this Figure. Hollow fiber dialyzer (1) is a standard dialyzer which is perfused, on the filtrate side, with dialysis fluid (9), entering the filter at inlet port (10a) and leaving it at outlet port (11a). The hollow fiber membranes (3a) of dialyzer (1), represented here as a single fiber, do not allow the passage of essential amounts of albumin, but serve to remove water-soluble components from the blood (6) which are also be removed from the blood when using the dialyzer for the treatment of renal failure patients.
Figure 2:
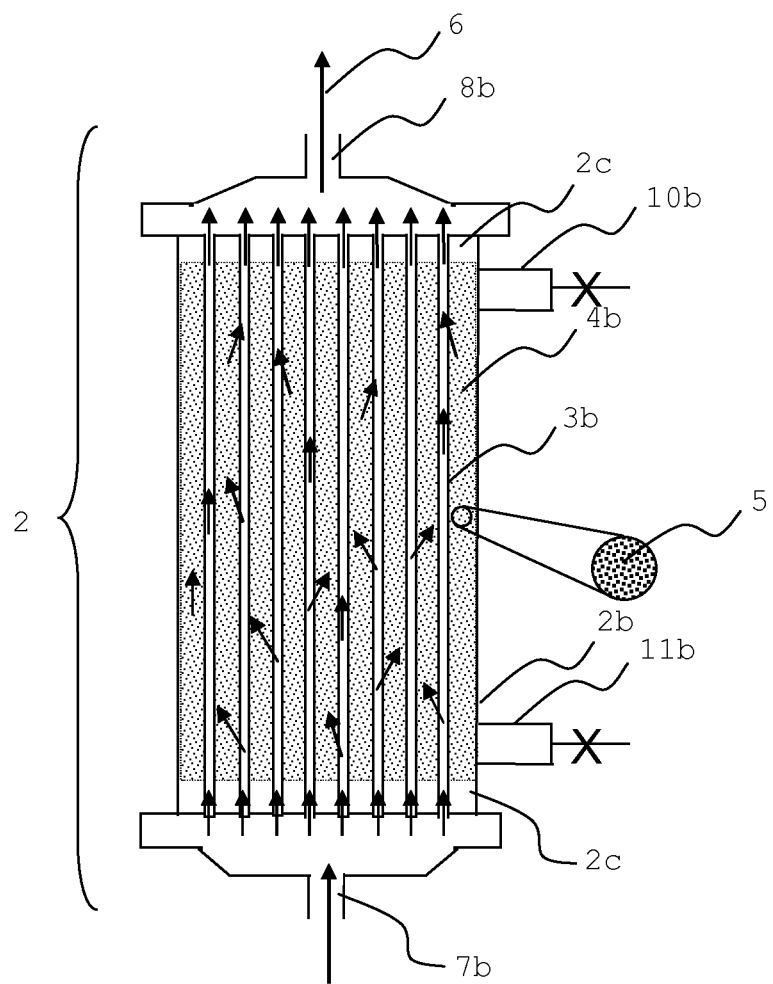
FIG. 2 shows another schematic representation of the hollow fiber membrane dialyzer (2) which is a component of the extracorporeal liver support system of the invention. The hollow fiber membrane dialyzer (2) comprising a cylindrical filter housing (2b), a bundle of essentially parallel hollow fibers (3b) distributed longitudinally within said housing (2b), wherein the open ends of the hollow fibers are in fluid communication with an inlet (7b) and an outlet (8b) means, and wherein the ends are embedded in a sealing compound (2c) such that the open ends of the hollow fibers (3b) extend through the sealing compound (2c). The dialyzer further comprises a filtrate space (4b), which is closed off from the lumen space of the hollow fiber membranes (3b). The filtrate space (4b) may optionally be in fluid communication with an inlet means (10b) and an outlet means (11b) for removing permeate from the housing (2b), but will generally be closed. The filtrate space (4b) is homogenously populated with particulate adsorbent material (5) being capable of interacting with components of the permeate, for example with liver toxins which maybe unbound or bound to albumin. In the present representation, the blood (6) which is derived from the patient enters the dialyzer (2) at inlet (7b) and leaves the dialyzer (2) at outlet (8b). Optional inlet (10b) and outlet (11b) are closed.
Figure 6:
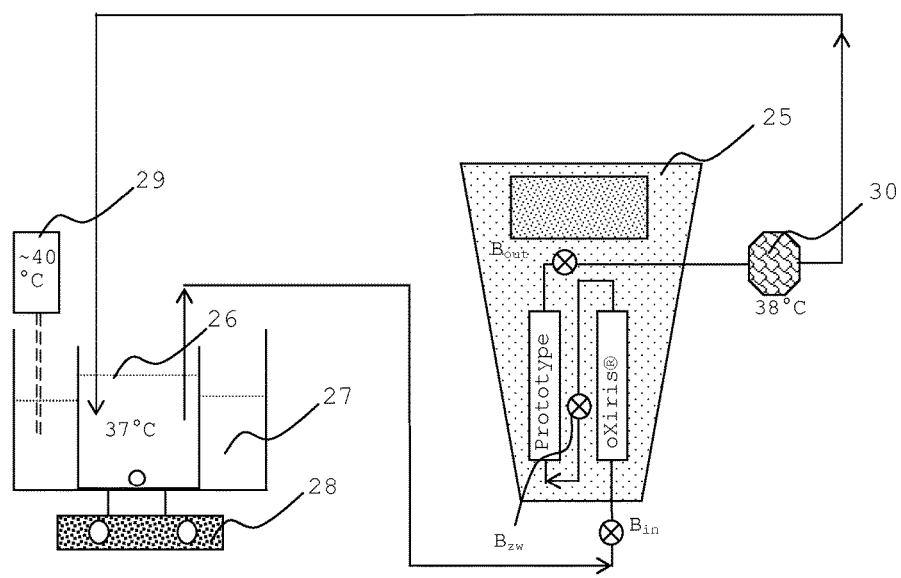
FIG. 6 shows a setup for the in vitro testing of the liver support system according the invention. The setup is recirculating and comprises, for example, a PrismafleX® (Gambro Lundia AB, Sweden) dialysis machine (25), and a blood warmer unit (30) which is set to 38° C. An oXiris® set is used for providing dialyzer (1), which is connected to a Prototype (dialyzer (2)) according to Example 2. The system further comprises a test solution pool (26), consisting of human plasma which is complemented with conjugated and unconjugated bilirubin, chenodeoxycholic acid, creatinine and ammonium chloride (see Example 3) which is warmed up in a water bath (27) to about 37° C. with a heater (29). The pool is stirred with the help of a magnetic stirrer (28). Samples can be taken at $B_{in}$, $B_{ZW}$ or $B_{out}$ in order to measure the concentration of the test substances before, between and after having passed the dialyzers.

The liver support system according to the invention (see FIG. 1) was tested in a re-circulating test setup (FIG. 6) comprising the Prototypes of Example 2 as dialyzer (2) and an oXiris® filter (Gambro) as dialyzer (1) on a PrismafleX® machine (Gambro). The test pool of 3000 ml contained 75 or 375 mg/l conjugated bilirubin (Sigma), 25 or 125 mg/l unconjugated bilirubin $M_W$ 842.9 (Calbiochem), 100 or 1000 mg/l chenodeoxycholic acid (CDCA) (Sigma), 1000 mg/l creatinine anhydrous (Sigma-Aldrich) and 20 mg/l ammonium chloride >99.5% (Roth) in Octaplas® LG human plasma (blood group 0, from Octapharma) which is kept at about 37° C. The respective higher concentrations were used for Prototypes 6, 7 and 9 (see FIGS. 7-10). The pool further contained 5 ml heparin (Heparin-Natrium-25000-ratiopharm). 60 ml 0.1M HCl were added to reach a neutral pH. The pool was protected from light at all times. The dialyzers were connected to the machine as prescribed and run in CVVHDF mode. The oXiris® dialyzer (1) was run from bottom to top. A blood warmer (PrismaTherm® II)

was connected downstream and set to 38° C. The system was flushed with 2×21 NaCl 0.9% comprising 5000 IU/l heparin. $Q_B$=200 ml/min, $Q_D$=1.5 l/h and replacement fluid 1 l/h (total: 2.5 l/h). UF=0 l/h. The system was run for 10 h. After that the filter and bloodlines were flushed with NaCl 0.9%. Samples of 3×1.5 ml were taken after 0 min, 10 min, 30 min, 60 min, 90 min, 120 min, 2 h, 3 h, 4 h, 4.25 h, 5 h, 6 h, 7 h, 8 h, 8.25 h, 9 h and 10 h at $B_{in}$, $B_{zw}$, and $B_{out}$, respectively. 1 ml heparin was added after 60 min and then after every other hour. Plasma solution (100 ml) was added after 4 h and 8 h, containing 18.75 mg conjugated bilirubin, 6.25 mg unconjugated bilirubin, 25 mg chenodeoxycholic acid, 250 mg creatinine and 60 mg ammonium chloride. This "spike" was omitted in some cases as indicated in the Figures. The dialysis solution used was Prismasol® 2 (Gambro).

The samples obtained during the tests were analyzed. The bilirubin samples were evaluated with the Bilirubin Auto Direct FS test kit from DiaSys Diagnostic Systems GmbH, Germany, for conjugated bilirubin, and with the ABX Pentra Bilirubin Total CP test kit from HORIBA ABX SAS, France, for total bilirubin. The CDCA concentrations were determined with the help of the Bile Acid Kit from Trinity Biotech (St. Louis, USA). The ammonium chloride concentrations were determined with the Enzytec® fluid Ammonia test kit from scil Diagnostics GmbH (Viernheim, Germany). Creatinine concentrations were determined with the help of the Creatinine Enzymatic PAP Kit from Dialab (Sasbach a. K., Germany).

Figure 7A:
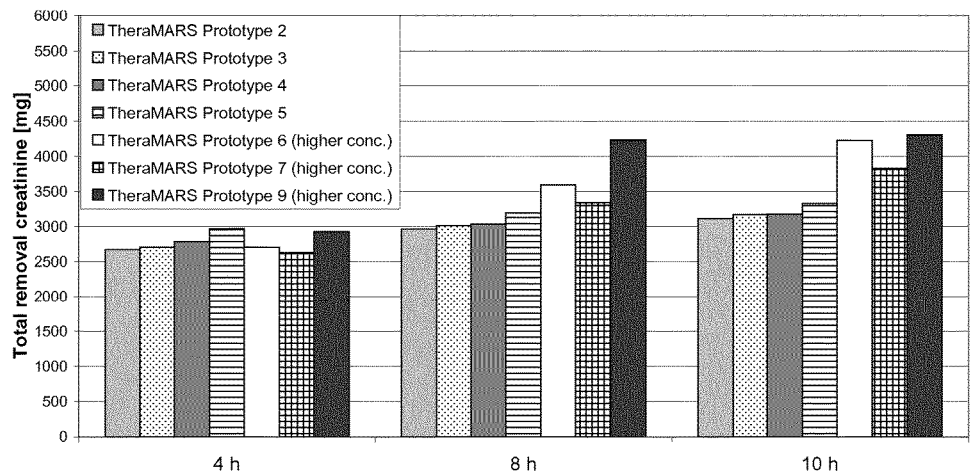
FIG. 7A depicts the total removal of creatinine in mg after 4, 8 and 10 hours.
Figure 7B:
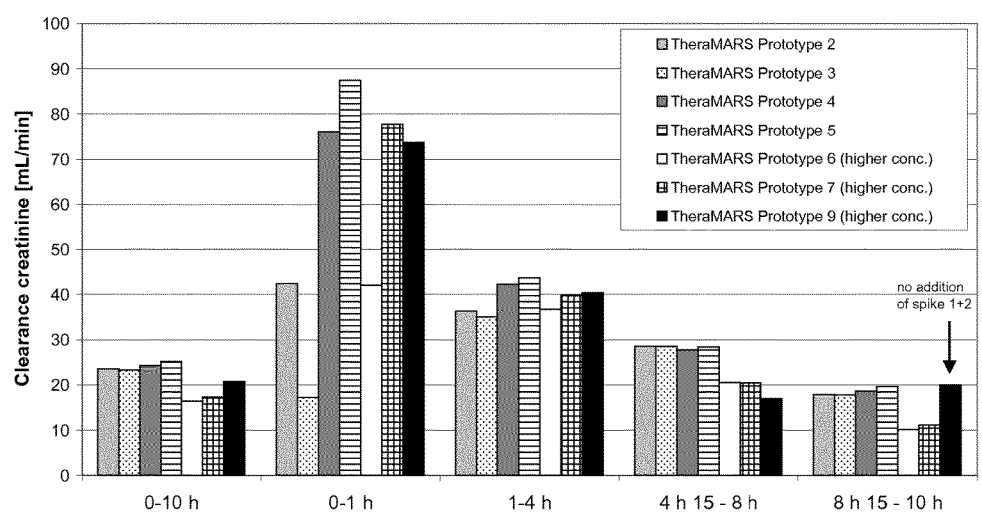
FIG. 7B shows the clearance data for creatinine in ml/min. Various time windows are shown for describing the clearance characteristics of the system over time.
Figure 8A:
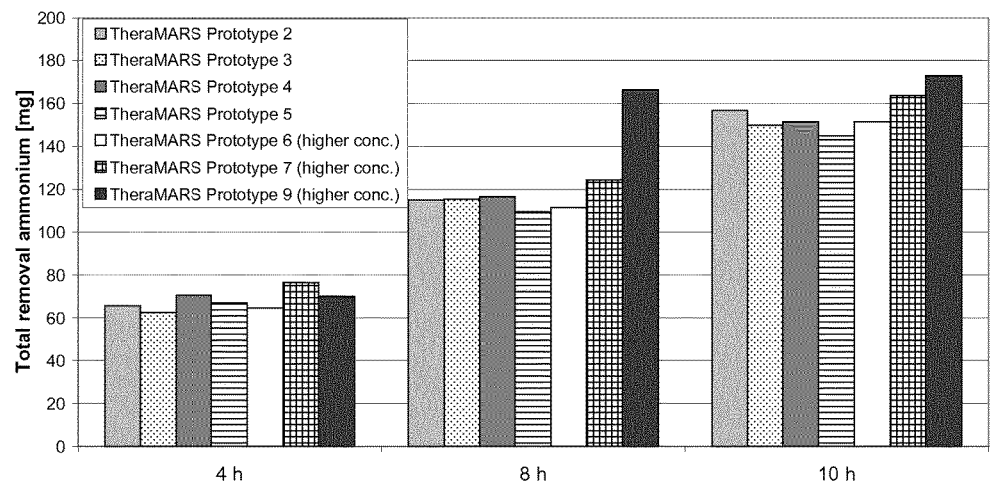
FIG. 8A depicts the total removal of ammonium in mg after 4, 8 and 10 hours.
Figure 8B:
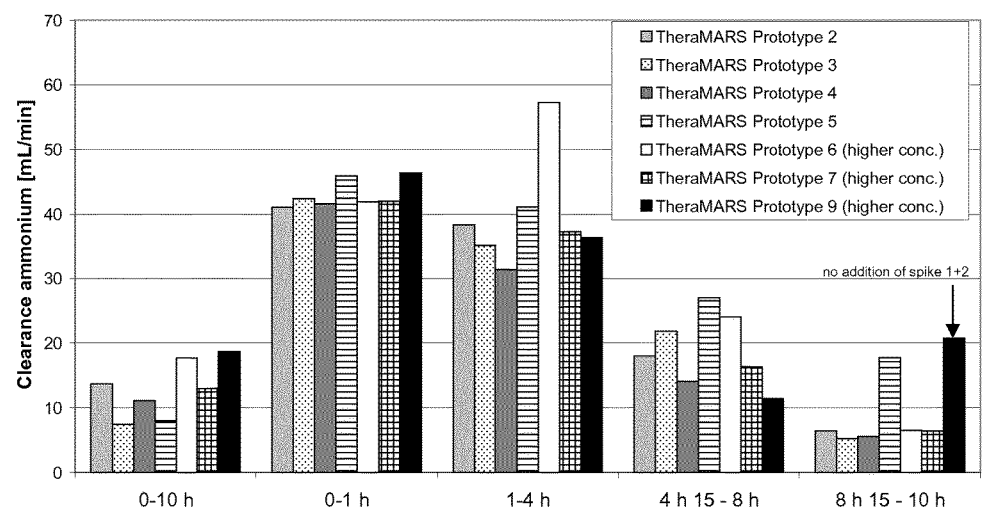
FIG. 8B shows the clearance data for creatinine in ml/min. Various time windows are shown for describing the clearance characteristics of the system for ammonium over time.
Figure 9A:
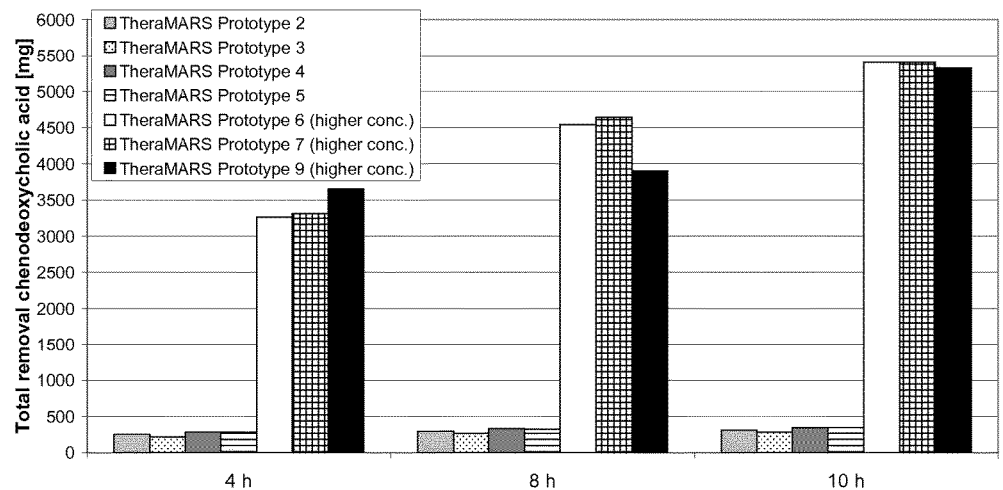
FIG. 9A depicts the total removal of CDCA in mg after 4, 8 and 10 hours.
Figure 9B:
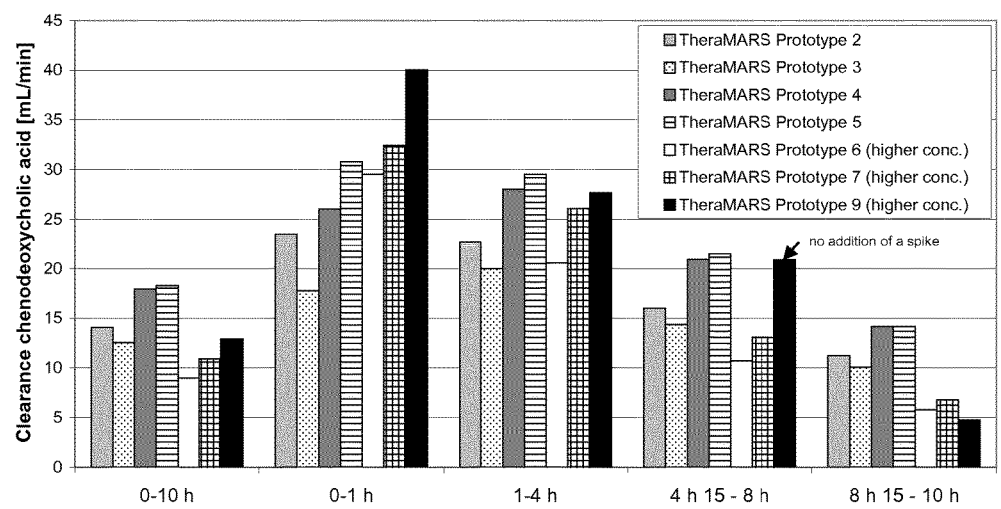
FIG. 9B shows the clearance data for creatinine in ml/min. Various time windows are shown for describing the clearance characteristics of the system over time.
Figure 10A:
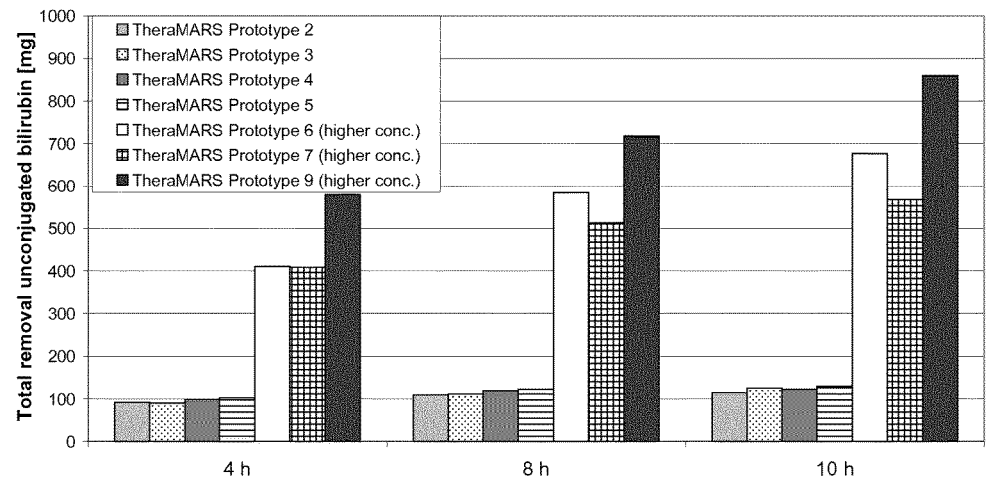
FIGS. 10A and B depict the total removal of unconjugated and conjugated bilirubin in mg after 4, 8 and 10 hours, respectively.
Figure 10B:
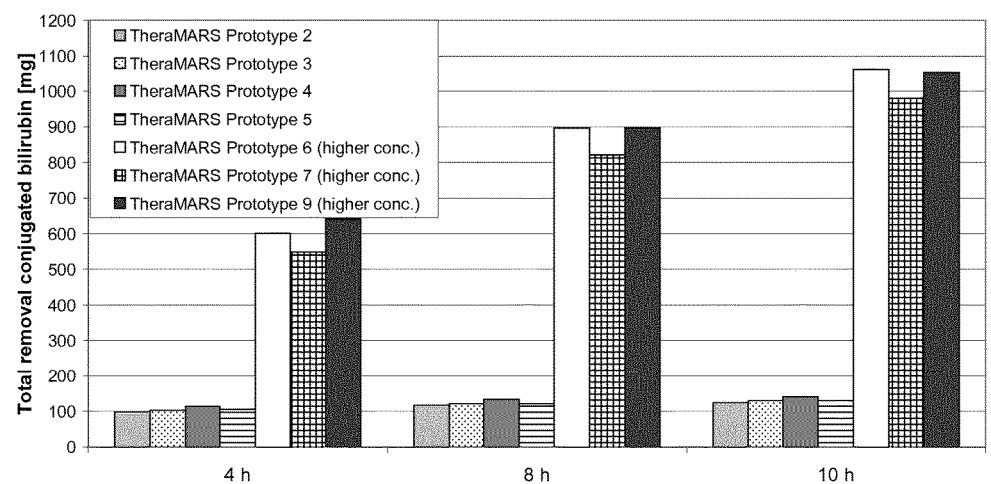
FIG. 10 shows the results for the removal of bilirubin which have been obtained in Example 3 with a test setup according to FIG. 6.
FIG. 10C shows the total removal of total bilirubin in mg after 4, 8 and 10 hours.
FIGS. 10D, E and F show the clearance data for unconjugated, conjugated and total bilirubin in ml/min, respectively. Various time windows are shown for describing the clearance characteristics of the system.
Figure 10C:
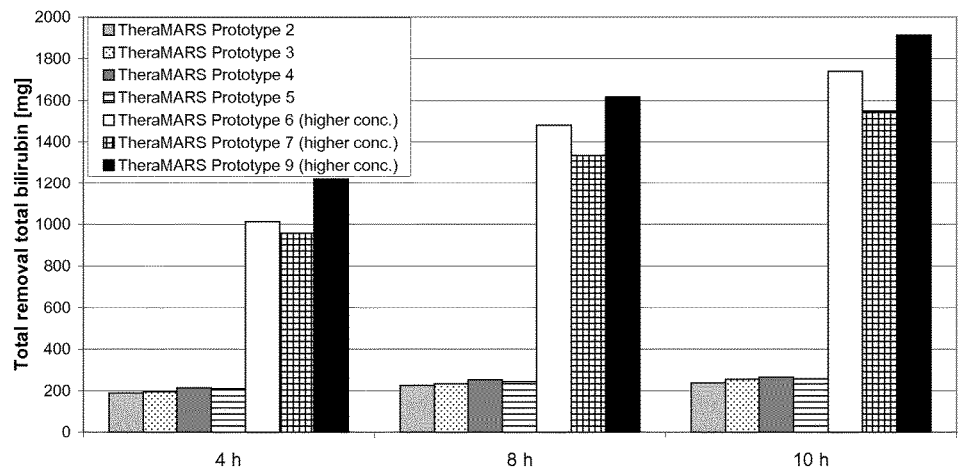
Figure 10D:
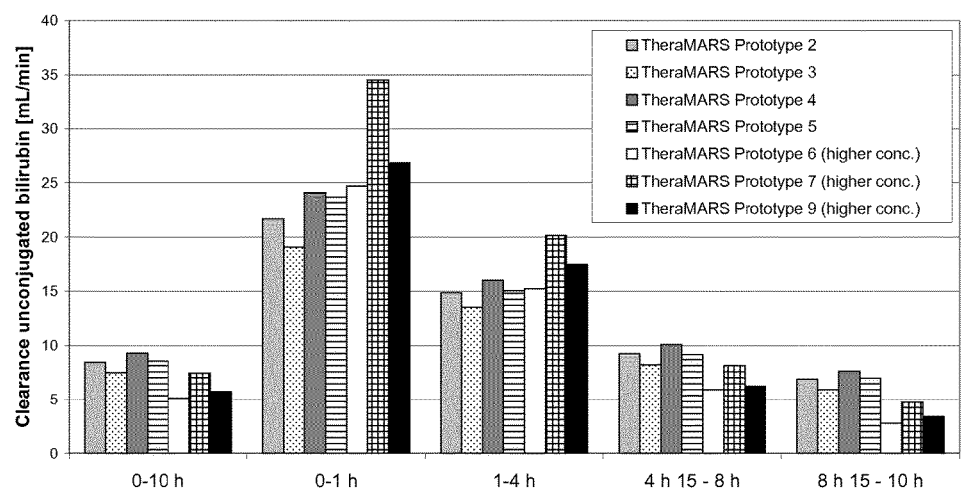
Figure 10E:
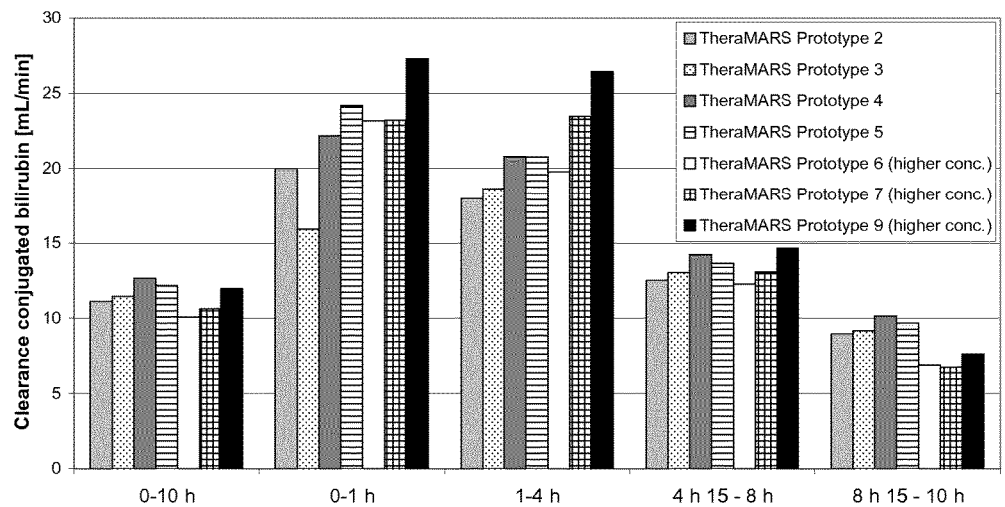
Figure 10F:
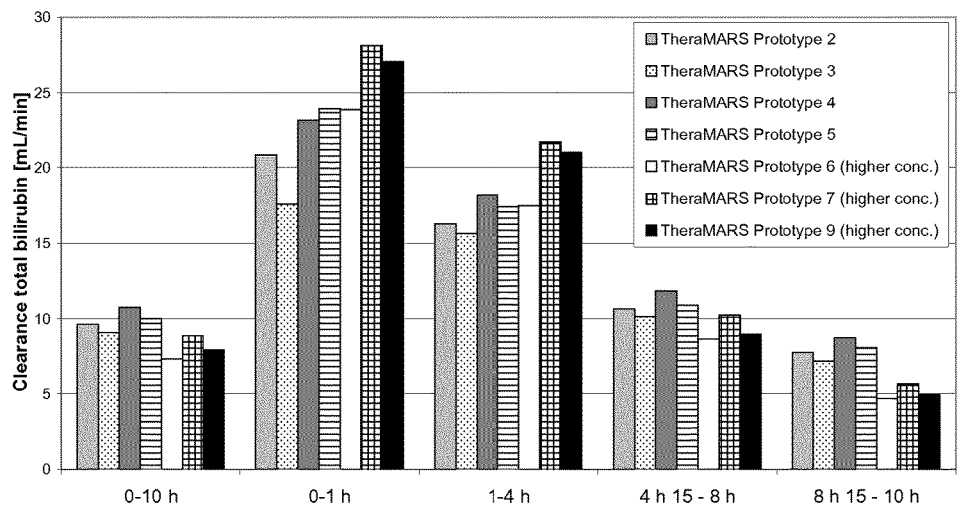

The results for the total removal of creatinine (in mg) are shown in FIG. 7A. The creatinine clearance is shown in FIG. 7B. The results for the total removal of ammonium (in mg) are shown in FIG. 8A. The ammonium clearance is shown in FIG. 8B. The results for the total removal of CDCA (in mg) are shown in FIG. 9A. The CDCA clearance is shown in FIG. 9B. Finally, FIG. 10A shows the total removal (in mg) of unconjugated bilirubin; FIG. 10B shows the total removal (in mg) of conjugated bilirubin (in mg). FIG. 10C shows the total removed amount of bilirubin (unconjugated and conjugated) in mg. The clearance for unconjugated and conjugated as well as the clearance of total bilirubin (unconjugated and conjugated) is shown in FIGS. 10D, 10E and 10F, respectively.

The invention claimed is:

1. A liver support device for conducting blood purification on a patient suffering from liver failure, comprising
   (a) a first hollow fiber membrane dialyzer comprising i) a first hollow fiber membrane and ii) a first filtrate space, wherein the first hollow fiber membrane dialyzer does not allow passage of an essential amount of albumin over a wall of the first hollow fiber membrane, wherein the first hollow fiber membrane dialyzer is perfused with the patient's blood, and wherein dialysate solution is passed in a continuous flow through the first filtrate space in a direction opposite to the blood flow within hollow fibers of the first hollow fiber membrane,
   (b) a second hollow fiber membrane dialyzer comprising i) a second hollow fiber membrane and ii) a second filtrate space, wherein the second hollow fiber membrane dialyzer allows passage of essential amounts of albumin over a wall of the second hollow fiber membrane, wherein the second filtrate space is closed off from a lumen space of the second hollow fiber membrane and is not perfused with any dialysis solution; and
   (c) a particulate material comprising at least one adsorbent,
   wherein the second filtrate space of the second hollow fiber membrane dialyzer is homogenously populated with the particulate material with a filling ratio of between 0.6 and 1.0, wherein the filling ratio is the volume in ml of the maximal amount of particulate material which can be accommodated in the filtrate space of a given hollow fiber membrane module ($V_{PM}$) and the utilizable volume in ml of the filtrate space of said module ($V_{FS}$):

$$\text{Filling ratio} = \frac{V_{PM}(\text{ml})}{V_{FS}(\text{ml})}$$

wherein $V_{PM}$ represents the volume of the particulate material which can be accommodated in the filtrate space of the module, and $V_{FS}$ represents the utilizable filtrate space, and wherein $V_{PM}$ is calculated from $$V_{PM}(\text{ml}) = \frac{m_{PM}(\text{g})}{\rho(\text{g/ml})}$$

wherein $m_{PM}$ represents the amount of particulate material which can be accommodated in the filtrate space of the module and $\rho$ represents the tapping density of the particulate material according to DIN ISO 3953.

2. A liver support device according to claim 1 wherein the second hollow fiber membrane of the second hollow fiber membrane dialyzer has a molecular weight cut-off in water, based on dextran sieving coefficients, of between 170 kilodaltons (kD) and 320 kD and a molecular weight retention onset in water, based on dextran sieving coefficients, of between 10 (kD) and 20 kD.

3. A liver support device according to claim 1 wherein the first hollow fiber membrane has a molecular weight cut-off in water, based on dextran sieving coefficients, of between 25 (kD) and 65 kD and a molecular weight retention onset in water, based on dextran sieving coefficients, of between 5 (kD) and 10 kD.

4. A liver support device according to claim 1 wherein the first hollow fiber membrane comprises at least one hydrophobic polymer and at least one hydrophilic polymer, wherein the at least one hydrophobic polymer is chosen from the group consisting of polyarylethersulfone (PAES), polypropylene (PP), polysulfone (PSU), polycarbonate (PC), polyacrylonitrile (PAN), polyamide (PA), polytetrafluorethylene (PTFE) or combinations thereof, and the at least one hydrophilic polymer is chosen from the group consisting of polyvinylpyrrolidone (PVP), polyethyleneglycol (PEG), polyvinylalcohol (PVA), and copolymer of polypropyleneoxide and polyethyleneoxide (PPO-PEO), or comprises a copolymer of acrylonitrile and sodium methallyl sulfonate.

5. A liver support device according to claim 1 wherein the first hollow fiber membrane comprises at least one hydrophobic polymer and at least one hydrophilic polymer, wherein the at least one hydrophobic polymer is chosen from the group consisting of polyarylethersulfone (PAES), polypropylene (PP), polysulfone (PSU), polycarbonate (PC), polyacrylonitrile (PAN), polyamide (PA), polytetrafluorethylene (PTFE) or combinations thereof, and the at least one hydrophilic polymer is chosen from the group consisting of polyvinylpyrrolidone (PVP), polyethyleneglycol (PEG), polyvinylalcohol (PVA), and copolymer of polypropyleneoxide and polyethyleneoxide (PPO-PEO).

6. A liver support device according to claim 1 wherein the second hollow fiber membrane allows passage of substances having a molecular weight of up to 45 kD with a sieving coefficient measured in whole blood of between 0.1 and 1.0, wherein the substances are selected from the group consisting of bilirubin, bile acids, aromatic amino acids, metabolites of aromatic amino acids, medium-chain fatty acids and cytokines.

7. A liver support device according to claim 1 wherein the second hollow fiber membrane has a molecular weight cut-off in water, based on dextran sieving coefficients, of between 170 (kD) and 320 kD and a molecular weight retention onset in water, based on dextran sieving coefficients, of between 15 (kD) and 20 kD.

8. A liver support device according to claim 1 wherein the second hollow fiber membrane dialyzer is located downstream from the first hollow fiber membrane dialyzer.

9. A liver support device according to claim 1 wherein the particulate material is one of hydrophobic and hydrophilic and is chosen from the group consisting of oxygen-containing adsorbents, carbon-based adsorbents and polymer-based adsorbents or combinations thereof.

10. A liver support device according to claim 9 wherein the hydrophobic particulate material is chosen from the group consisting of activated carbon, carbon nanotubes, hydrophobic silica, styrenic polymers, polydivinylbenzene polymers and styrene-divinylbenzene copolymers.

11. A liver support device according to claim 10 wherein the hydrophilic particulate material comprises one of:
  a combination of at least one activated carbon, at least one copolymer of styrene and divinylbenzene without any functional groups and at least one copolymer of styrene and divinylbenzene carrying trimethylbenzyl ammonium functional groups; and
  a combination of at least one copolymer of styrene and divinylbenzene without any functional groups and at least one copolymer of styrene and divinylbenzene carrying trimethylbenzyl ammonium functional groups.

12. A liver support device according to claim 1 wherein the second hollow fiber membrane comprises at least one hydrophobic polymer and at least one hydrophilic polymer, wherein the at least one hydrophobic polymer is chosen from the group consisting of polyarylethersulfone (PAES), polypropylene (PP), polysulfone (PSU), polycarbonate (PC), polyacrylonitrile (PAN), polyamide (PA), polytetrafluorethylene (PTFE) or combinations thereof, and the at least one hydrophilic polymer is chosen from the group consisting of polyvinylpyrrolidone (PVP), polyethyleneglycol (PEG), polyvinylalcohol (PVA), and copolymer of polypropyleneoxide and polyethyleneoxide (PPO-PEO), or comprises a copolymer of acrylonitrile and sodium methallyl sulfonate.

13. A liver support device according to claim 1 wherein the second hollow fiber membrane comprises at least one hydrophobic polymer and at least one hydrophilic polymer, wherein the at least one hydrophobic polymer is chosen from the group consisting of polyarylethersulfone (PAES), polypropylene (PP), polysulfone (PSU), polycarbonate (PC), polyacrylonitrile (PAN), polyamide (PA), polytetrafluorethylene (PTFE) or combinations thereof, and the at least one hydrophilic polymer is chosen from the group consisting of polyvinylpyrrolidone (PVP), polyethyleneglycol (PEG), polyvinylalcohol (PVA), and copolymer of polypropyleneoxide and polyethyleneoxide (PPO-PEO).

14. A hollow fiber membrane dialyzer comprising
(i) a bundle of hollow fiber membranes having a molecular weight cut-off in water, based on dextran sieving coefficients, of between 170 (kD) and 320 kD and a molecular weight retention onset in water, based on dextran sieving coefficients, of between 10 (kD) and 20 kD, and wherein the hollow fiber membranes comprise a lumen space and a filtrate side,
(ii) a filtrate space which is closed off from the lumen space of the hollow fiber membranes, and
(iii) a particulate material which is located on the filtrate side of the hollow fiber membrane dialyzer, wherein the particulate material comprises at least one adsorbent chosen from the group consisting of oxygen-containing adsorbents, carbon-based adsorbents and polymer-based adsorbents and combinations thereof; and
wherein the hollow fiber membrane dialyzer is the second hollow fiber membrane dialyzer of claim 1 for use in a liver support device according to claim 1 for the removal of liver toxins from fluids in extracorporeal therapies.

15. A hollow fiber membrane dialyzer comprising
(i) a bundle of hollow fiber membranes having a molecular weight cut-off in water, based on dextran sieving coefficients, of between 170 (kD) and 320 kD and a molecular weight retention onset in water, based on dextran sieving coefficients, of between 10 (kD) and 20 kD, and wherein the hollow fiber membranes comprise a lumen space and a filtrate side,
(ii) a filtrate space which is closed off from the lumen space of the hollow fiber membranes, and
(iii) a particulate material which is located on the filtrate side of the hollow fiber membrane dialyzer, wherein the particulate material comprises at least one adsorbent chosen from the group consisting of oxygen-containing adsorbents, carbon-based adsorbents and polymer-based adsorbents and combinations thereof; and
wherein the hollow fiber membrane dialyzer is the second hollow fiber membrane dialyzer of claim 1 for use in a liver support device according to claim 1 for the removal of protein bound liver toxins from fluids in extracorporeal therapies.

16. A hollow fiber membrane dialyzer comprising
(i) a bundle of hollow fiber membranes having a molecular weight cut-off in water, based on dextran sieving coefficients, of between 170 (kD) and 320 kD and a molecular weight retention onset in water, based on dextran sieving coefficients, of between 10 (kD) and 20 kD, and wherein the hollow fiber membranes comprise a lumen space and a filtrate side,
(ii) a filtrate space which is closed off from the lumen space of the hollow fiber membranes, and
(iii) a particulate material which is located on the filtrate side of the hollow fiber membrane dialyzer, wherein the particulate material comprises at least one adsorbent chosen from the group consisting of oxygen-containing adsorbents, carbon-based adsorbents and polymer-based adsorbents and combinations thereof,
wherein the filtrate space is homogenously populated with the particulate material with a filling ratio of between 0.6 and 1.0, wherein the filling ratio is the volume in ml of the maximal amount of particulate material which can be accommodated in the filtrate space of a given hollow fiber membrane module ($V_{PM}$) and the utilizable volume in ml of the filtrate space of said module ($V_{FS}$):

$$\text{Filling ratio} = \frac{V_{PM}(\text{ml})}{V_{FS}(\text{ml})}$$

wherein $V_{PM}$ represents the volume of the particulate material which can be accommodated in the filtrate space of the module, and $V_{FS}$ represents the utilizable filtrate space, and wherein $V_{PM}$ is calculated from $$V_{PM}(\text{ml}) = \frac{m_{PM}(\text{g})}{\rho(\text{g/ml})}$$

wherein $m_{PM}$ represents the amount of particulate material which can be accommodated in the filtrate space of the module and $\rho$ represents the tapping density of the particulate material according to DIN ISO 3953.

* * * * *